United States Patent
Bouwmeester et al.

(10) Patent No.: US 7,214,507 B2
(45) Date of Patent: May 8, 2007

(54) PLANT ENZYMES FOR BIOCONVERSION

(75) Inventors: Hendrik Jan Bouwmeester, Renkum (NL); Jan-Willem de Kraker, Jena (DE); Marloes Schurink, Ede (NL); Raoul John Bino, Wageningen (NL); Aede de Groot, Wageningen (NL); Maurice Charles R. Franssen, Wageningen (NL)

(73) Assignee: Plant Research International B.V., Wageningen (NL)

( * ) Notice: Subject to any disclaimer, the term of this patent is extended or adjusted under 35 U.S.C. 154(b) by 0 days.

(21) Appl. No.: 10/489,762

(22) PCT Filed: Sep. 17, 2002

(86) PCT No.: PCT/NL02/00591

§ 371 (c)(1),
(2), (4) Date: Sep. 7, 2004

(87) PCT Pub. No.: WO03/025193

PCT Pub. Date: Mar. 27, 2003

(65) Prior Publication Data

US 2005/0019882 A1 Jan. 27, 2005

(30) Foreign Application Priority Data

Sep. 17, 2001 (EP) .................................. 01203519

(51) Int. Cl.
*C12P 1/00* (2006.01)
*A61K 36/28* (2006.01)

(52) U.S. Cl. .................. 435/41; 560/249; 424/736; 424/773; 424/725

(58) Field of Classification Search ..................... None
See application file for complete search history.

(56) References Cited

U.S. PATENT DOCUMENTS 6,200,786 B1 * 3/2001 Huang et al. ............... 435/132
6,451,576 B1 * 9/2002 Croteau et al. ............. 435/232

OTHER PUBLICATIONS

Dedeyan B et al. 2000. Appl Env Microbiol 66: 925-929.*
Yoder OC et al. 2001. Curr Opin Plant Biol 4: 315-321.*
Nielsen KA et al. 2005. Cytochrome P450s in plants. In Cytochrome P450: structure, mechanism, and biochemistry, 3$^{rd}$ ed., Ortiz de Montellano, ed. p. 553.*
Bohlmann, Jorg, et al., "Plant terpenoid synthases: Molecular biology and phylogenetic analysis", *Proc. Natl. Acad. Sci.* 1998, 95:4126-4133.
de Kraker, Jan-Willem, et al., "Biosynthesis of Germacrene A Carboxylic Acid in Chicory Roots. Demonstration of a Cytochrome P450 (+)-Germacrene A Hydroxylase and NADP$^+$-Dependent Sesquiterpenoid Dehydrogenase(s) Involved in Sesquiterpene Lactone Biosynthesis", *Plant Physiology* 2001, 125:1930-1940.
de Kraker, Jan-Willem, et al., "Germacrenes from fresh costus roots", *Phytochemistry* 2001, 58:481-487.
de Kraker, Jan-Willem, et al., "(+)-Germacrene A Biosynthesis", *Plant Physiol.* 1998, 117:1381-1392.
Halkier, Barbara Ann, "Catalytic Reactivities and Structure/Function Relationships of Cytochrome P450 Enzymes", *Phytochemistry* 1996, 43(1):1-21.
Schuler, Mary A., "Plant Cytochrome P450 Monooxygenases", *Critical Reviews in Plant Sciences* 1996, 15(3):235-284.

* cited by examiner

*Primary Examiner*—Sandra E. Saucier
*Assistant Examiner*—Lora E Barnhart
(74) *Attorney, Agent, or Firm*—Hoffmann & Baron, LLP

(57) ABSTRACT

The invention provides a method for converting sesquiterpene. The method includes reacting a sesquiterpene substract with a sesquiterpene converting enzyme. The enzyme is from a species or organism containing sesquiterpenes. The sesquiterpene substrate is not naturally present in the species or organism.

5 Claims, 20 Drawing Sheets

β-terpineol (R=OH)
β-terpinyl acetate (R=OAc)

α-terpineol (R=OH)
α-terpinyl acetate (R=OAc)

R = H (digitoxin)
R = OH (digoxin)

(-)-α-cububene       (-)-α-gurjunene       germacrone       limonene (+)-costunolide (5)

PLANT ENZYMES FOR BIOCONVERSION

This application is the U.S. National Phase of International Application Number PCT/NL02/00591 filed on 17 Sep. 2002, which is incorporated herein by reference.

BACKGROUND OF THE INVENTION

The invention relates to the field of bioconversion, using plant enzymes for the production of flavor, fragrance, pharmaceutical or bio-control agents from less valuable substrates. More specifically it relates to a process for production of terpenoid compounds by the use of plant enzymes.

Modern chemistry strongly depends on the use of catalysts in order to have efficient and clean reactions with a minimum of waste. Especially the use of biocatalysts (enzymes, cells) is strongly increasing, also in industry. The most important features of biocatalysts are (Faber, 2000):

1. they are very efficient;
2. they are environmentally acceptable;
3. they operate under mild conditions;
4. they are selective.

Up to now, the large majority of enzymes used in bioconversion employing biocatalysis for industrial and laboratory applications is obtained from microbial sources. A minor fraction of enzymes is obtained from plant sources (Faber, 2000). Nevertheless, the plant kingdom is an important source for the chemist and the biotechnologist because plants produce a unique variety of chemicals (Franssen and Walton, 1999). The rationale for this is simple: there is no way plants can escape from their predators, so they have to defend themselves by chemical ways. Plants make compounds with the most fantastic chemical structures: the antitumor drug TAXOL® (paclitaxel) (from *Taxus brevifolia*), the insect feeding deterrent azadirachtin (from the Indian neem tree *Azadirachta indica*) and the analgesic morphine (from *Papaver somniferum*). It is mainly because of the tremendous importance of compounds like these that science has been, and still is, interested in the application of plant cells and enzymes, irrespective of the disadvantages they sometimes have (Walton and Brown, 1999). By far the most important group of secondary metabolites, containing a vast number of components that act as flavor, fragrance, pharmaceutical or bioactive (insecticidal, anti-microbial, repellent, attractant, etc, etc) compounds, are the terpenoids. The terpenoids belong to the isoprenoids. By definition isoprenoids are made up of so-called isoprene (C5) units. This can be recognized in the number of C-atoms present in the isoprenoids which usually can be divided by five (C5, C10, C15, C20, C25, C30 and C40), although also irregular isoprenoids (e.g. C13, C16) and polyterpenes (Cn) have been reported.

The terpenoids consist of a.o. monoterpenes, sesquiterpenes, diterpenes, triterpenes, tetraterpenes and polyterpenes (rubbers), etc. Mono- and sesquiterpenes, the C10 and C15 branch of the isoprenoid family, are economically interesting as flavor and fragrance compounds in foods and cosmetics, and can have anti-carcinogenic effects and antimicrobial properties. Mono- and sesquiterpenes have also been shown to be of ecological significance, for instance in the interaction and signaling between plants, plants and insects/spider mites and plants and microorganisms.

The sesquiterpene lactones are an important subgroup of the sesquiterpenes, and over 4000 differentstructures have been identified. A wealth of information is available about the structural aspects and biological activities of these type of compounds (e.g. Picman, 1986; Harborne et al., 1999; Seigler, 1995).

Sesquiterpene lactones may constitute up to 5% of the dry weight of the plant and occur mainly in members of the Asteraceae (in about 450 species), the largest of all plant families, but also occur in other higher plant families such as the Apiaceae (12 species) and lower plants such as liverworts, for examnple the genus *Frullania* (Harborne et al., 1999). Sesquiterpene lactones may occur throughout a plant, but are most commonly associated with leaves, flower parts and taproots.

The Asteraceae contain 1317 genera and 21000 species. They are mainly herbaceous plants, sometimes shrubs or trees, usually with a taproot, sometimes with tubers. Many of the Asteraceae contain (essential) oil bearing organs, such as ducts or trichomes, some of them contain latex. The Asteraceae contain many economic and ornamental plants, such as Sunflower (*Helianthus annuus*; for the production of seeds and sunflower oil), Jerusalem-Artichoke (*Helianthus tuberosus*; of which the tubers are eaten and that is also used for the fructan production), and *Artemisia annua* (for the production of the effective anti-malarial artemisinin. Also used as food are the roots of Salsify (*Tragopogon porrifolius*) and Scorzonera (*Scoizonera hispanica*), the young flower-heads of Globe Artichoke (*Cynara scolymus*), and the leaves of Lettuce (*Lactuca sativa*), Endive (*Cichorium endiva*) and Radicchio and Brussels Endive (*Cichorium intybus*). In addition, there are many ornamental Asteraceae, for example in the genera *Dahlia, Doronlicum, Heleniumn, Tagetes, Helianthus, Aster, Centaurea, Gerbera*, etc.

The occurrence of sesquiterpene lactones in the tribes of the Asteraceae is of taxonomic interest. They are common in the Heliantheae, occur frequently in the Anthemideae, Cichorieae; Cynareae, Senecioneae, Inuleae and Vernonieae, only infrequently in the Eupatoriaea and not in the Astereae, Mutisieae, Tageteae and Arcoteae-Calenduleae (Seigler, 1995). Crop species that have been shown to contain sesquiterpene lactones are for example: Artichoke, Lettuce, Endive, Radicchio, Brussels Endive, Sunflower, Jerusalem Artichoke, *Artemisia annua, Matricaria recutita*. Some wild (or ornamental) Asteracea species containing sesquiterpene lactones are: *Lactuca virosa, Achillea* spp., *Ambrosia* spp. *Cnicus benedictus, Artemisia* spp., *Xanthium* spp., *Iva axillaris, Parthenium* spp., *Helenium* spp., *Hymenoxys odorata, Vernonia* spp., *Vanillosmopsis* spp., *Eremanthus* spp., *Moquinea* spp., *Parthenium* spp., *Arnica* spp., *Atractylodis macrocephala, Eupatorium cannabium, Achillea millefolium, Tanacetum* (*Chrysanthemum*) *vulgare, Inula helenium* and *Taraxacum officinale* (Seigler, 1995; Van Genderen et al., 1996).

One example of an Asteraceous species that contains large amounts of sesquiterpene lactonesis Chicory. The roots of chicory are extremely bitter, due to these sesquiterpene lactones.

Chicory is a blue-flowered composite plant that has spread all over the world from the Mediterranean and east Asia. Since the seventeenth century it has been cultivated (var. *sativum*) for its bitter roots that were roasted and used in hot 'coffee-like' beverages. While the use of its roots was displaced by genuine coffee from *Coffea arabica*, sprouts of chicory (var. *foliosum*) that are grown in the dark became popular as a vegetable (Belgian endive) halfway through the nineteenth century. Nowadays it is a common crop in Belgium, northern France and The Netherlands (Weeda et al., 1991; Vogel et al., 1996). During the first year of growth, the plant develops a deep taproot and produces a rosette of leaves on a short stem. Following a period of cold exposure, the plant develops a floral meristem. Commercial production involves harvesting the plant following the attainment of a proper stage of maturity of the root, followed by floral bud induction (cold storage) and then an accelerated but controlled development of the floral axis and surrounding basal leaves in the dark (forcing). The end product of forcing is a chicon, a small white head of leaves ringed with regions of yellow-green. This Belgian endive is known for its slightly bitter taste originating from sesquiterpene lactones (Pyrek, 1985; Seto et al., 1988; van Beek et al., 1990; Price et al., 1990). The major sesquiterpene lactones of chicory are guaianolides, but smaller amounts of eudesmanolides and germacranolides are also present. The bitter taste of chicory is in particular associated with the presence of the guaianolides lactucin, 8-deoxylactucin, and lactucopicrin.

Although a lot of information is available about the structural aspects and biological activities of the sesquiterpene lactones, little is known about their biosynthesis. By far the largest group of naturally occurring sesquiterpene lactones is the group of germacranolides, and the majority of sesquiterpene lactones are thought to evolve from this group. The simplest member of the germacranolides, (+)-costunolide, is generally accepted as the common intermediate of all germacranolide-derived lactones (Geissman, 1973; Herz, 1977; Fischer et al., 1979; Seaman, 1982; Song et al., 1995).

(+)-Costunolide was first isolated from costus roots (Saussurea lappa Clarke) by Paul et al. (1960) and Somasekar Rao et al. (1960), and has since been found with other sesquiterpene lactones in various plants (Fischer et al., 1979). Amongst them is lettuce (Lactuca sativa), a species that is closely related to chicory and also contains the bitter tasting compounds lactucin and lactucopicrin (Takasugi et al, 1985; Price et al., 1990).

Recently we have demonstrated that the sesquiterpenoid backbone of the sesquiterpene lactones in chicory is formed by a (+)-germacrene A synthase which cyclizes FPP to (+)-germacrene A (de Kraker et al., 1998; Bouwmeester et al., 1999b). This (+)-germacrene A is not further transformed into a guaiane or a eudesmane skeleton, indicating that functionalization of the molecule precedes its cyclization. Studies on the biosynthesis of santonin (Barton et al., 1968) suggested that lactone formation precedes any other oxidation of the sesquiterpenoid ring system (Cordell, 1976), and various authors have proposed a biosynthetic route from (+)-germacrene A (8) toward (+)-costunolidce ((Geissman, 1973; Herz, 1977; Seaman, 1982; Fischer, 1990; Song et al., 1995). In this hypothetical route (+)-germacrene A is hydroxylated to germacra-1(10),4,11(13)trien-12-ol that is further oxidized via germacra-1(10),4,11(13)-trien-12-al to germacra-1(10),4,11(i3)-trien-12-oic acid. The germacrene acid is thought to be hydroxylated at the $C_6$-position and subsequent loss of water leads to the formation of a lactone ring such as present in (+)-costunolide.

Unfortunately, germacrenes are notoriously unstable compounds, susceptible to proton-induced cyclizations and heat induced (e.g. steam distillation, GC-analysis) Cope rearrangement (Takeda, 1974; Bohlman et al., 1983; Reichardt et al., 1988; Teisseire, 1994; de Kraker et al, 1998). None of the intermediates between (+)-germacrene A and (+)-costunolide has ever been isolated, apart from germacra-1(10),4,11(13)-trien-12-al that was isolated with greatest difficulty from Vernonia glabra and could not be separated from its cyclization product costal (Bohlman et al, 1983). Probably as a result of this instability, the hypothetical biosynthetic route for (+)-costunolide has merely been based on the isolation from costus roots of the Cope-rearrangement products (−)-elema-1,3,11(13)-trien-12-ol and (−)-elema-1,3,11(13)-trien-12-al, and the proton-induced cyclization products costol, costal and costic acid (Bawdekar and Kelkar, 1965; Bawdekar et al., 1967; Maurer and Grieder, 1977).

The next step in the biosynthesis of sesquiterpene lactones is catalysed by a cytochrome P450 enzyme (D)e Kraker et al., 2001). Cytochrome P450 enzymes ($M_r$=±50,000) mostly catalyzes oxidation reactions, but also reductions. Most vertebrate genomes contain more than 30 different structural genes for cytochromes P450 (Mathews and van Holde, 1996), maiing this a large and diverse protein family. These proteins resemble mitochondrial cytochrome oxidase in being able to bind both $O_2$ and CO. Cytochromes P450, however, strongly absorb light at 450 nm when they are in the reduced state and complexed with CO. Light of 450 nm displaces CO from the heme, hence CO binding is photoreversible. For this reason, cytochrome P450 enzymes exhibit photoreversible inhibition by CO (Donaldson and Luster, 1991). Plant cytochrome P450 monooxygenase systems are associated with the endoplasmic reticulum or a prevacuole, and consequently are located in the light membrane (microsomal) fraction of the cell.

Cytochrome P450 enzymes are involved in the hydroxylation of a large variety of compounds. There are two classes of cytochrome P450 activities known: those involved in biosynthetic routes and those involved in detoxification of xenobiotics (Donaldson and Luster, 1991; Mihaliak et al., 1993; Schuler, 1996). These reactions include the hydroxylations of steroid hormone biosynthesis, and the synthesis of hydroxylated fatty acids and fatty acid epoxides. In addition, cytochromes P450 act upon thousands of xenobiotics, including drugs such as phenobarbital and environmental carcinogens such as benzopyrene, a constituent of tobacco smoke. Hydroxylation of foreign substances usually increases their solubility and is a step in their detoxification, or metabolism and excretion.

Cytochrome P450 systems participate in a wide variety of additional reactions, including epoxidation, peroxygenation, desulfuration, dealkylation, deamination, and dehalogenation. These reactions are particularly active in the liver, where a number of cytochromes P450 are xenobiotic-inducible; that is, their synthesis is stimulated by substrates that are metabolized by these enzymes (Mathews and van Holde, 1996). Inducers include drugs such as phenobarbital and other barbiturates.

The amino acid residues that constitute the active site of the enzyme determine the specificity of a given P450. They can vary widely between different cytochromes P450; however, the principal component of the active site of all these enzymes is a heme moiety. The iron ion of the heme moiety is the site of the catalytic reaction, and is also responsible for the strong 450 nm absorption peak in combination with CO. The substrate specificity of cytochrome P450 enzymes depends on their function in the organism: the biosynthesis of metabolites or the breakdown of xenobiotics in animals. The enzymes that take care of the breakdown of xenobiotics have a low specificity, so that a few enzymes can protect the organism against a large diversity of xenobiotics. How the detoxification of xenobiotics in plants is accomplished is not clear yet. Enzymes that are involved in biosynthetic routes of metabolites in plants or animals in general have a very high substrate specificity (Donaldson and Luster, 1991; Mihaliak et al., 1993; Schuler, 1996).

Many different enzymes are involved in the biosynthetic pathways of complex plant metabolites. The enzymes catalyse, among others, stereo- and regioselective hydroxylations, (ep)oxidations, reductions, glycosylations, esterifications and cyclisations. Especially the enzymes that are involved in hydroxylations and oxidations have great potential in chemistry, since the corresponding chemical transformations involve the use of toxic reagents and halogenated solvents, which is undesirable because of safety and environmental reasons (March, 2001). For example, allylic hydroxylations are usually performed using selenium dioxide in methylene chloride (Jerussi 1970). The direct introduction of a carbonyl function next to a carbon-carbon double bond requires the use of toxic chromium trioxide (March, 2001) or the expensive and highly toxic ruthenium tetroxide (e.g., Petit and Furstoss, 1995). Furthermore, hydroxylating and oxidizing enzymes usually have far greater regio- and stereoselectivity than the chemical reagents. A few examples are given below.

Partly on account of their importance in fragrance and flavour industries, the hydroxylation and further biotransformation of terpenoids has been particularly well studied, using cell cultures of essential oil producing species and of other plants, such as *Nicotiana tabacum* (Suga and Hirata, 1990). Stereospecificity was shown, for example, by the formation of only trans isomers from hydroxylation occurring at C4 of β-terpineol and its acetate and by the predominant formation of a trans-diol as a result of hydroxylation of the endocyclic double bond of α-terpinyl acetate (FIG. 4).

Digitoxin is a cardiac glycoside from *Digitalis* sp. Its β-hydroxylation on the 11-position yields the more potent digoxin. This has been achieved by purified, reconstituted and immobilized digitoxin 12β-hydroxylase (a cytochrome P450 enzyme complex) from *Digitalis lanata* in a bioreactor (Petersen and Seitz, 1988; Petersen et al., 1987).

Sesquiterpene alcohols and ketones are an interesting group of compounds for a number of reasons. Sesquiterpene alcohols, for example have been shown to be involved in resistance against micro-organisms: the Solanaceae for example produce sesquiterpene alcohol phytoalexins upon infection with pathogenic fungi and in vitro assays have shown that these sequiterpene alcohols have a strong antifugal activity. Also a number of sesquiterpene alcohols are important in the flavor and fragrance industry, for example santalol, typical for the very expensive sandalwood essential oil, and khusimol, patchoulol, etc. Also the sesquiterpene ketone, nootkatone is a commercially important compound. Because of its excellent organoleptic qualities and in particular its typical grapefruit taste, nootkatone is a widely used ingredient in perfumery and the flavor industry. Nootkatone was also shown to inhibit gastric lesion which explains that it is a constituent of some stomach medications (Yamahara et al., 1990). Although nootkatone can be obtained from valencene or other substrates using chemical synthesis (Hunter and Brogden, 1965; Wilson and Shaw, 1978; Canadian patent no 901601; M. Pesaro et al., 1968; Birch, 1974; U.S. Pat. No. 5,847,226) there is a large demand for natural nootkatone. At present, such a quality can only be obtained by extraction of natural products containing nootkatone, in particular grapefruit, a method which is hardly economic. With the enzymes lignin peroxidase (from *Phanerochaete chrysosporium*) and lactoperoxidase it is possible to convert (+)-valencene into nootkatone under certain conditions. In this way, the conversion is very low and is most probably due to singlet oxygen that is formed by these two enzymes (Willershausen and Graf, 1991). Several microorganisms, bacteria and fungi, were also screened for their capability to transform (+)-valencene into nootkatone all without much success. (Balfoort, 1994).

Two bacteria of the genus *Enterobacter* from a Dutch soil and an infected local beer were isolated by enrichment cultures on (+)-valencene. These bacteria transformed (+)-valencene into nootkatone (12% yield) and many other valencene derivatives (Dhavlikar and Albroscheit, 1973). Also other methods for the bioconversion of valencene to nootkatone using inicro-organisms have been studied, but none of these methods have proven commercially viable (Dhavlikar et al., 1973; Drawert et al., 1984).

SUMMARY OF THE INVENTION

The invention relates to the field of bioconversion, using oxidising enzymes, in particular cytochrome P450 related enzymes, with high regio- and enantioselectivity, for the production of flavor, fragrance, pharmaceutical or bio-control agents from less valuable substrates. More specifically it relates to a process for production of bioactive terpenoid compounds by the use of plant enzymes.

The invention provides the use of enzymes derived from an organism, in particularly from a plant, that contains sesquiterpene lactones, in biocatalysis. The regio- and stereoselective oxidation of organic compounds is still a largely unresolved challenge to organic chemistry (Faber, 2000). We investigated whether the oxidising enzymes of a sesquiterpene containing organism such as an Asteraceae species, are capable of converting for example sesquiterpene olefins to commercially interesting products. We found useful enzymes with a surprisingly broad application. Asteraceae, but also plant species from other families, that contain sesquiterpene lactones also contain the enzymes required for their biosyntheis, and thus can be used as a preferred source for these enzymes. In a preferred embodiment, the invention provides an enzyme that is useful for nootkatone synthesis. Nootkatone is a compound mainly founds in grapefruits and other citrus fruits. Surprisingly, however, we provide here evidence that nootkatone synthesis can also occur with an enzyme that is not derived from a citrus fruit, but from another sesquiterpene containing species instead. Considering the large availability of non-citrus derived enzymes, for example from the large amounts of chicory taproots that remain after the growing of the chicory vegetable or inuline chicory, or from other Asteraceae species, such as lettuces, sunflower, artichoke, radicchio, etc, etc, that can easily and abundantly be grown, we have provided here useful enzymes for for example the flavor, aroma, pharmaceutical or biocide industry. In addition to the Asteraceae, the liverworts (Hepaticae) are another good example of a cheap and widely available source for these oxidising enzymes and several families of the liverworts have been reported to contain sesquiterpene lactones. Sesquiterpene lactones isolated from higher plants contain, essentially without exception, α-methylene-γ-lactone groups in which H-7 is α-oriented. The liverworts produce sesquiterpene lactones of the enantiomeric series. Nevertheless, the oxidising enzymes from these organisms can carry out similar reactions as the enzymes from higher plants and are a valuable addition to the higher-plant enzymes. In particular, the invention provides a method for converting a substrate and generating a stereo- and regioselective conversion product comprising subjecting said substrate to enzymes derived from a plant species producing sesquiterpene lactones, especially wherein said conversion product comprises an alcohol, aldehyde/ketone or carboxylic acid: Also, the conversion products can be further modified using commercial enzymes such as alcohol dehydrogenases or microbial bioconversion systems. Considering that useful Asteraceae and liverwort species can easily be grown, the invention provides an inexpensive resource of enzymes or other biocatalysts (cells, explants, tissue, hairy roots or cell cultures) for bioconversion. Particularly useful crops comprise *Cichorium* spp, lettuces such as *Lactuca* spp., *Helianthus* spp. etc. but are not limited to these. The method as provided herein allows the conversion of a terpene in a useful stereo- and regioselective conversion product, for example linear or branched terpene alcohols, aldehydes/ketones or carboxylic acids, especially where said substrate comprises a sesquiterpene. In particular, a method is provided wherein said enzyme comprises a cytochrome P450 monooxygenase, such as (+)-germacrene A hydroxylase or a sesquiterpenolide C2 hydroxylase These enzymes catalyse the hydroxylation of (+)-germacrene A and a sesquiterpene lactone intermediate in chicory sesquiterpene lactone biosynthesis. Although the enzymes belong to a biochemical pathway, they do not have a high substrate specificity. Hydroxylation of a sesquiterpene occurs when the compound contains, like germacrene A, an isopropenyl substituent or, like germacrene B, an isopropylidene substituent or like valencene an allylic C2-position. The conversion carried out by these hydroxylases occurs with high regio- and stereoselectivity which is a big advantage compared with microbial hydroxylations which usually occur with very low specificity. In the detailed description, examples are given for the conversion of valencene to the commercially important flavor/fragrance compound nootkaton. The substrate, (+)-valencene, is converted to several products; two of them are valencene alcohol (2.61%) and nootkatone (24.4%). Nootkatone is used as a constituent of soft drinks and perfumes. Also, a method is provided wherein the substrate amorpha-4,11-dien-12-ol, is converted to the antimalarial artemisinin or a precursor thereof. Other substrates that were hydroxylated include germacrene A, as one might expect, the substrate with the highest rate of conversion and β-selinene. Alternative substrates that are converted to their corresponding alcohols are: alloisolongifolene (at 1.49% compared to β-selinene). Amorphadiene is converted to two products, at 74.0 and 18.7%; the first is amorpha-4,11-dien-12-ol the precursor of artemisinin and the identity of the latter is unknown. The relative rate of conversions of the other substrates were found to be the following: (−)-α-trans-bergamotene (13.5%), (−)-β-elemene (56.2%), germacrene A (110%, probably even higher), germacrene B (3.13% and 8.60%, cis-trans isomers), (+)-γ-gurjunene (54.9%), (+)-ledene (7.20%), and neointermedeol (6.92%). It is particularly useful when said enzymes are derived from an extract of said Asteraceae species, extracts being easily made according to a method known in the art. It is also contemplated herein to use free latex from an Asteraceae as enzyme preparation. In the detailed description, examples are given with enzymes derived from chicory roots. Because the roots of chicory are extremely bitter, they are regarded as a waste product of chicory cultivation. About 100,000 tons of chicory roots are produced annually in The Netherlands, but because of their bitter taste, it is not even possible to use them as cattle feed. Therefore they provide a vast and cheap source for the enzymes described in the invention. For an industrial process, the invention provides a method to make enzyme extracts that contain the P450 enzymes. These can be prepared by homogenising chicory roots in an extraction buffer according to Example 1 containing PVPP. The resulting slurry is then filtered and centrifuged. Low- (20,000×g) followed by high-speed (150,000×g) centrifugation will result in highly-enriched microsomal pellets, but also supernatants obtained after very low speed (for example 2,000×g) centrifugation are active, making it easier to adapt the procedure for industrial processes. The pellets or supernatants can be resuspended in a suitable assay buffer to which the appropriate substrates, and NADPH or an NADPH-regenerating system can be added or the enzymes may be immobilised according to Example 5 to increase their efficiency and lifetime. Cofactor recycling will further increase the economic feasability. After incubation at a suitable temperature, the alcohol products can be easily extracted and separated from the substrate using preparative-scale column chromatography. The suitable substrates can be any sesquiterpene hydrocarbon that could yield an interesting product after hydroxylation at positions equivalent to the positions described in the examples, for example valencene, amorphadiene, (−)-α-trans-bergamotene, γ-gurjunene, ledene, germacrene A, germacrene B, but not limited to those. The corresponding alcohols formed enzymatically from these substrates could be further oxidised to the corresponding aldehydes/ketones or acids—if these are of more value—using a chicory alcohol and aldehyde dehydrogenase or commercially available dehydrogenases. However, another possible method is provided wherein said enzymes are present in a tissue- or cell culture derived from said Asteraceae species, for example a hairy root culture. Hairy root and cell cultures of chicory can be obtained using standard protocols (hairy root cultures: Song et al., 1995; cell cultures: Dubois et al., 1988). The cultures are supplied with sesquiterpenes such as valencene, amorphadiene, (−)-α-trans-bergamotene, γ-gurjunene, ledene, germacrene A, germacrene B, but not limited to those, preferably at 200–1000 mg/l. After one week of growth in the presence of the sesquiterpenes, the reaction products are extracted from the culture medium and the hairy roots/cells. It is also possible to make use of a recombinant enzyme, for example derived from a transgenic plant or micro-organism provided with a nucleic acid encoding an enzyme according to the invention. According to the invention, cytochrome P450 cDNAs can be obtained using random sequencing of a cDNA library of chicory taproots, the organ where the activity of these enzymes is highest. Also a PCR approach is feasible where the sequence homology of cytochrome P450 enzymes is used to design degenerate primers that can be used to generate PCR fragments. These fragments are used to screen a cDNA library to obtain full-length cDNAs. These cDNAs can be expressed in *E. coli*, yeast or any other micro-organism adapted to large-scale industrial fermentation and suitable for the expression of P450s. In such a fermentation procedure, the transgenic micro-organisms will be fed the desired sesquiterpene hydrocarbon substrates for example valencene, amorphadiene, (−)-α-trans-bergamotene, γ-gurjunene, ledene, germacrene A, germacrene B, but not limited to those. The produced alcohol products can be extracted continuously or in batch. These micro-organisms could also be equipped with the synthase of the desired sesquiterpene hydrocarbon substrate, such as for example the valencene synthase, which would further reduce the costs of production, and an alcohol and/or aldehyde dehydrogenase in order to produce ketones/aldehydes, such as in the case of nootkatone production, or acids—when required.

The invention also provides a conversion product obtainable by a method according to the invention. In particular interesting products are (E)-trans-bergamota-2,12-diene-14-ol, the direct precursor of the corresponding aldehyde with sandalwood-like fragrance properties, and a number of novel conversion products such as alloisolongifolene alcohol, amorpha-4,11-diene-12-ol germacrene B alcohol, 5,11 (13)-guaiadiene-12-ol and a ledene alcohol, all alcohols that have not been reported before. With the invention larger amounts of these alcohols can be produced to confirm their identity and to investigate their properties as flavor and fragrance compounds, pharmaceuticals or biocides, or of their corresponding aldehydes/ketones and carboxylic acids.

Also, the invention provides an isolated or recombinant enzyme or enzyme extract derived from an Asteraceae species capable of converting a substrate and generating a conversion product after subjecting said substrate to said enzyme(s) and use of such enzyme(s) or extract according to the invention in biocatalysis, for example for the generation of a flavor or fragrance compound, pharmaceutical or biocide. The invention thus provides for example the use of micro-organisms, expressing genes encoding said oxidising enzymes that were isolated from sesquiterpene lactone producing plant species for bioconversion. Also the use of micro-organisms, expressing genes encoding said oxidising enzymes that were isolated from sesquiterpene lactone producing plant species in combination with genes that introduce the formation of said substrates in the micro-organism and hence the formation of said oxidised bioconversion products is provided herein. Also the invention provides the use of transgenic sesquiterpene lactone producing plant species, such as chicory, expressing genes that introduce the formation of said substrates in planta, such as terpene synthase genes that introduce the formation of said terpenes in planta and hence the formation of said oxidised bioconversion products or expressing a valencene synthase that introduces the formation of valencene in planta and hence the formation of nootkatone, or expressing amorpha-4,11-diene synthase that introduces the formation of amorpha-4,11-diene in planta and hence the formation of artemisinin or its precursors, or expressing α-trans-bergamotene synthase that introduces the formation of α-trans-bergamotene in planta and hence the formation of (E)-trans-bergamota-2,12-dien-14-ol.

DETAILED DESCRIPTION OF THE INVENTION

TABLE I

Figure 1:
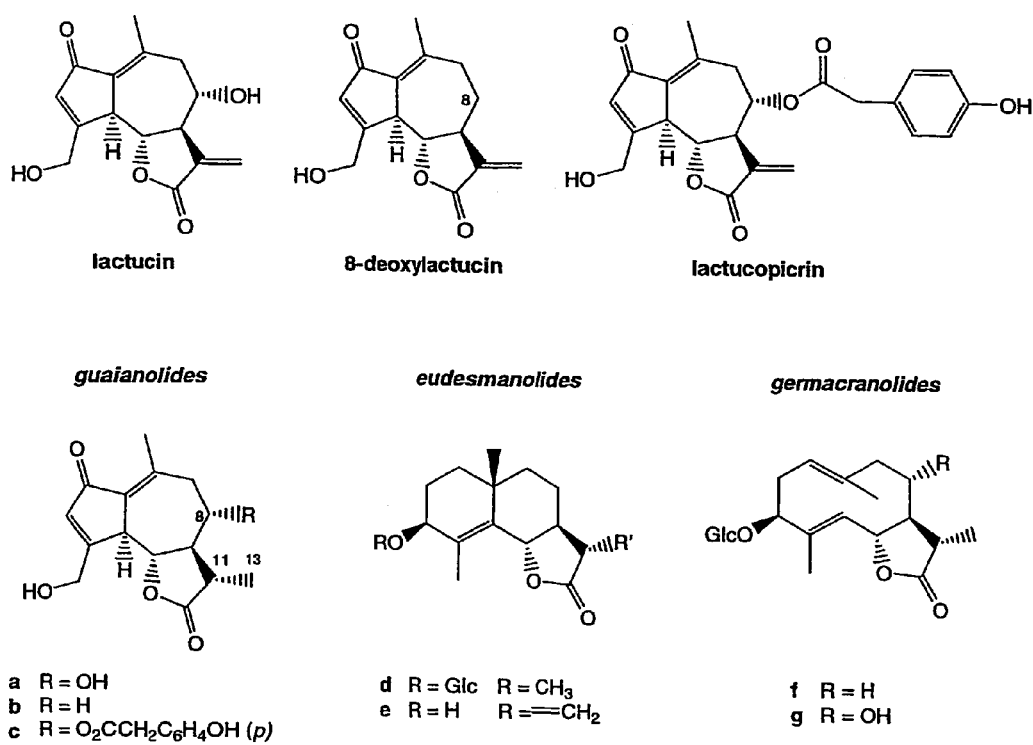
FIG. 1. Bitter principles of chicory. The guaianolides lactucin, 8-deoxylactucin and lactucopicrin are major compounds. Minor sesquiterpene lactones of chicory are the guaianolides 11(S), 13-dihydrolactucin (a), 11(S), 13-dihydro-8-deoxylactucin (b), 11(S),13-dihydrolactucopicrin, (c); the eudesmanolides sonchuside C (d) and cichoriolide A (e), and the germacranolides sonchuside A (f) and cichorioside C (g).

Conversion of sesquiterpenes by a microsomal pellet of chicory in the presence of NADPH.

| Substrate Structure | KI | Product(s) Structure | KI | Relative conversion$^a$ |
|---|---|---|---|---|
| alloisolongifolene | 1409 | alloisolongifolene alcohol* | 0<br>1688 | 1.5 ± 0.1 |
| amorpha-4,11-diene | 1482 | amorpha-4,11-diene-12-ol* | 1650 | 74.0 ± 2.8 |
|  |  | amorpha-4,11-diene alcohol | 1720 | 18.7 ± 1.2 |
| (−)-α-trans-beramotene | 1440 | (E)-trans-bergamota-2,12-dien-14-ol* | 1720 | 13.5 ± 0.2 |

TABLE I-continued

Conversion of sesquiterpenes by a microsomal pellet of chicory in the presence of NADPH.

| Substrate Structure | KI | Product(s) Structure | KI | Relative conversion[a] |
|---|---|---|---|---|
| (−)-β-elemene | 1397 | (−)-elema-1,3,11(13)-trien-12-ol* | 1673 | 56.2 ± 2.6 |
| (+)-germacrene A | 1512[b] | germacra-1(10),4,11(13)-trien-12-ol* | 1673–1806[b] | 110.0 ± 5.1[c] |
| germacrene B | 1566[b] | germacrene B alcohol | 1694[d] and 1700[d] | 3.1 ± 0.1 8.6 ± 0.8 |
| (+)-γ-gurjunene | 1479 | 5,11(13)-guaiadiene-12-ol | 1760 | 54.9 ± 1.5 |
| (+)-ledene | 1504 | ledene alcohol | 1787 | 7.2 ± 0.4 |
| neointermedeol | 1631 | 4β-H-eudesm-11(13)-ene-4,12-diol | 1909 | 6.9 ± 2.4 |

TABLE I-continued

Conversion of sesquiterpenes by a microsomal pellet of chicory in the presence of NADPH.

| Substrate Structure | KI | Product(s) Structure | KI | Relative conversion[a] |
|---|---|---|---|---|
| (+)-β-selinene | 1492 | (+)-β-costol* | 1778 | 100 ± 4.5 |

[a]100% conversion corresponds to the hydroxylation rate of β-selinene that yields a β-costol peak-size of 6.3 × the internal standard (2.5 nmol cis-nerolidol in each assay).
[b]The Kovats' indices of these germacrene are determined at an injection port temperature of 150° C.; quantitative measurements are done on the basis of their Cope-rearrangements products measured at an injection port temperature of 250° C..
[c]This conversion rate is a summation of the peaks of elematrien-12-ol, costol, elematrien-12-al, and elematrien-12-oic acid.
[d]Kovats' indices were determined at an injection port temperature of 250° C. and probably belong to the Cope-rearrangement products.
→Hydroxylation probably occurs at one of these allylic positions.
Alcohols marked with an asterisk were identified using reference compounds.

TABLE II

Effect of the addition of 50 μM (+)-germacrene A or 50 μM (+)-α-Cubebene upon hydroxylation.

| | | Inhibition (%) ± SD | |
|---|---|---|---|
| Substrate | Product[a] | Germacrene A | α-Cubebene |
| alloisolongifolene | alloisolongifolene alcohol | 100.0 | 100.0 |
| amorpha-4,11-diene | amorpha-4,11-diene-12-ol | 84.9 ± 0.1 | −9.2 ± 2.5 |
| | amorpha-4,11-diene alcohol (KI 1720) | 84.9 ± 1.0 | −2.3 ± 1.5 |
| (−)-β-trans-bergamotene | (E)-trans-bergamota-2,12-dien-14-ol | 89.2 ± 1.8 | 30.2 ± 4.5 |
| (−)-β-elemene | (−)-elema-1,3,11(13)-trien-12-ol | 90.4 ± 1.2 | 19.5 ± 1.8 |
| germacrene B | germacrene B alcohol (KI 1694) | 100.0 | 32.6 ± 3.6 |
| | germacrene B alcohol (KI 1700) | 100.0 | 27.3 ± 10 |
| (+)-γ-gurjunene | (+)-γ-gurjunene alcohol | 88.0 ± 0.9 | −5.6 ± 0.2 |
| (+)-ledene | ledene alcohol | 100.0 | 35.5 ± 1.9 |
| neointermedeol | 4β-H-eudesm-11(13)-ene-4,12-diol | 67.5 ± 1.9 | 3.4 ± 4.5 |
| (+)-β-selinene | (+)-β-costol | 60.3 ± 3.4 | 0.4 ± 2.0 |

[a]The amount of sesquiterpene alcohol produced in control incubations is set at 100% and is comparable with those of Table I.

TABLE III

Effect of the used solvent for (+)-γ-gurjunene on enzyme activity

| Solvent | Enzyme activity[a] ± SD |
|---|---|
| hexane | <0.1 |
| pentane | 0.47 ± 0.07 |
| iso-propanol | 1.76 ± 0.16 |
| ethanol | 1.87 ± 0.01 |
| DMSO | 1.80 ± 0.09 |

[a]Peak height of γ-gurjunene alcohol relative to the internal standard (5 nmol cis-nerolidol)

TABLE IV

Requirements for (+)-costunolide synthase activity

| Addition | Percentage Enzyme Activity[a] ± SD |
|---|---|
| none | 0 ± 0 |
| 1 mM NADPH | 100 ± 8 |
| 1 mM NADH | 7 ± 2 |
| 1 mM NADPH + 1 mM NADH | 109 ± 23 |
| 1 mM NADP$^+$ + NAD$^+$ | 1 ± 1 |
| 1 mM NADPH + argon atmosphere | 0 ± 0 |

[a]100% enzyme activity corresponds to the summation of a dehydrosaussurea lactone, saussurea lactone, and leucodin peak size of respectively 0.35, 0.19, and 0.09 × internal standard (1 nmol cis-nerolidol in all assays).

TABLE V

Pyridine nucleotide cofactors dependency of 11(S),13-dihydrocostunolide and leucodin biosynthesis.

| | Percentage Enzyme Activity ± SD | |
|---|---|---|
| Pyridine Nucleotide Cofactor | Dihydrocostunolide (20) | Leucodin (22) |
| 1 mM NADPH | [a]100 ± 3 | [a]100 ± 10 |
| none | 15 ± 1 | 0 ± 0 |
| 1 mM NADH | 14 ± 2 | 0 ± 0 |
| 1 mM NADPH + 1 mM NADH | 107 ± 4 | 65 ± 19 |
| 1 mM NADP$^+$ + 1 mM NAD$^+$ | 18 ± 3 | 0 ± 0 |

[a]100% enzyme activity corresponds to an saussurea lactone and leucodin peak size of respectively 1.34 and 0.42 × internal standard (1 nmol cis-nerolidol in all assays).

TABLE VI

Inhibition experiments concerning biosynthesis of 11,13-dihydrocostunolide and leucodin.

| | Percentage Enzyme Activity ± SD | |
|---|---|---|
| Assay Conditions[a] | Dihydrocostunolide (20) | Leucodin (22) |
| Air (≈80% N$_2$ + 20% O$_2$) | [b]100 ± 9 | [b]100 ± 33 |
| 80% CO + 20% O$_2$ | 140 ± 4 | 8 ± 1 |
| Argon | 134 ± 6 | 0 ± 0 |
| Standard | [c]100 ± 3 | [c]100 ± 10 |
| Cytochrome C (100 µM) | 105 ± 5 | 0 ± 0 |
| DMSO (1%) | [d]100 ± 5 | [d]100 ± 10 |
| Metyrapone (100 µM) | 87 ± 11 | 70 ± 16 |
| Clotrimazole (10 µM) | 119 ± 9 | 0 ± 0 |
| Miconazole (10 µM) | 100 ± 5 | 0 ± 0 |
| Aminobenzotriazole (10 µM) | 75 ± 8 | 86 ± 33 |

[a]All incubations were carried out in the presence of 1 mM NADPH-regenerating system and flavins.
[b]100% enzyme activity corresponds to a saussurea lactone and leucodin peak size of respectively 1.63 and 0.34 × internal standard (1 nmol cis-nerolidol in all assays).
[c]100% enzyme activity corresponds to a saussurea lactone and leucodin peak size of respectively 1.34 and 0.42 × internal standard (1 nmol cis-nerolidol in all assays).
[d]100% enzyme activity corresponds to a saussurea lactone and leucodin peak size of respectively 1.43 and 0.18 × internal standard (1 nmol cis-nerolidol).

TABLE VII

Conversion of (+)-valencene by a microsomal pellet of chicory in the presence of NADPH.

| Substrate Structure | KI | Product(s) Structure | KI | Relative conversion[a] |
|---|---|---|---|---|
| (+)-valencene | 1500 | valencen-12-ol[e] | 1777 | 2.6 ± 0.1 |
| | | nootkatone | 1820 | 24.4 ± 1.1 |

[a]100% conversion corresponds to the hydroxylation rate of β-selinene that yields a β-costol peak-size of 6.3 × the internal standard (2.5 nmol cis-nerolidol in each assay).
[e]The mass spectrum of the detected compound was identical to the mass spectrum of valencene-12-ol provided by Firmenich SA (Switzerland).

Detailed Description

EXAMPLE 1

Bioconversion of Sesquiterpenes Using Enzymes Isolated from Chicory Roots

The ability of the germacrene A hydroxylase present in chicory roots to hydroxylate other substrates in addition to germacrene A was investigated. Fresh roots of cultivated-chicory (*Cichorium intybus* L., cv Focus) harvested during late summer were obtained from a grower in Veenendaal, The Netherlands. The chicory roots were cut into small pieces, frozen in liquid nitrogen, and stored at −80° C.

Materials and Methods (+)-Germacrene A was isolated from costus roots (De Kraker et al, 2001b). Alloisolongifolene, (−)-α-gurjunene, (+)-γ-gurjunene, and (+)-ledene were purchased from Fluka. ICN Biomedicals furnished (−)-α-cubebene. The compounds (−)-limonene and (+)-limonene were purchased from Merck and Janssen, respectively. Amorpha-4,11-diene was synthesised by Dr. B. J. M. Jansen (Bouwmeester et al., 1999a). Germacrone was isolated from the natural oil of *Geranium macrorrhizum* and germacrene B was synthesised by Dr. D. P. Piet (Piet et al., 1995).

(−)-α-trans-Bergamotene and (−)-β-elemene were a gift from Prof. W. A König (Hamburg University). Neointermedeol was synthesised by Dr. R. P. W. Kesselmans (Kesselmans, 1992). (+)-β-Selinene was isolated from celery oil and was a gift from Dr. T. A. van Beek. Substrates were dissolved at 10 mM concentrations in ethanol.

Alloisolongifolene alcohol was prepared from alloisolongifolene via its corresponding aldehyde by $SeO_2$, according to the protocol of Umbreit and Sharpless (1977). To a solution of 77 mg $SeO_2$ and 68 mg salicylic acid in 30 mL $CH_2Cl_2$, 100 mg alloisolongifolene was added. Stirring at room temperature turned the reaction mixture yellow and a red solid precipitated in the first few hours. The reaction was monitored by GC-MS along with TLC and was stopped by the addition of 60 mL demineralised water after 2.5 days. The reaction mixture was extracted with 45 mL ether, and the organic phase was subsequently washed with 30 mL brine. The red precipitate remained in the aqueous phase during extraction. After drying and evaporation, the organic phase yielded 214 mg of a crude solid that after flash chromatography on silica with pentane-$CH_2Cl_2$ (3:1) yielded 31 mg of alloisolongifolene aldehyde, a strong odorous compound (cedar-wood like). $^1$H NMR (200 MHz, $C_6D_6$) δ 0.71 (s, 3H, Me) δ 0.90 (s, 3H, Me), δ 0.93–2.04 (m, 13H), δ 5.42 (s, 1H, $CH_2$=C), δ 5.73 (s, 1H, $CH_2$=C), δ 9.35 (s, 1H, CH=O). $^{13}$C NMR (50 MHz, $C_6D_6$) δ 15.0 (q), δ 19.6 (q), δ 20.5 (t), δ 22.2 (t), δ 32.3 (t), δ 36.3 (t), δ 38.7 (t), δ 45.1 (t), δ 46.1 (s), δ 47.1 (s), δ 47.7 (s), δ 50.8 (d), δ 133.5 (t), δ 157.0 (s), δ 193.9 (d). EIMS (70 eV) m/z: 218 [M]$^+$ (41), 203 (48), 189 (32), 185 (30), 175 (42), 161 (68), 147 (53), 145 (37), 133 (35), 119 (46), 107 (42), 105 (80), 95 (33), 93 (46), 91 (100), 81 (37), 79 (65), 77 (64), 55 (43), 53 (34), 41 (74), 39 (45). Fifteen milligrams of the aldehyde was added to a solution of 1.8 mg $LiAlH_4$ in 0.5 mL ether. The grey suspension was stirred for 17.5 hours at room temperature and for an additional half our after the careful addition of one spatula $Na_2SO_4.10H_2O$. One and a half millilitre of demineralised water was added to the mixture that was subsequently 3 times extracted with 1 mL of ether. The ether was passed through glasswool-plugged Pasteur pipette filled with silica and a spatula tip of $MgSO_4$. The solvent was evaporated yielding 17 mg of alloisolongifolene alcohol. $^1$H NMR (200 MHz, $C_6D_6$) δ 0.77 (s, 3H, Me), δ 0.91 (s, 3H, Me), 0.96–1.63 (m, 13H), δ 3.96 (m, 2H), δ 4.95 (d, 1H, J=1.3 Hz) δ 5.30 (dd, 1H, J=3.26 Hz, 1.55 Hz). $^{13}$C NMR (50 MHz, $C_6D_6$) δ 15.1 (q), δ 19.7 (q), δ 20.7 (t), δ 22.3 (t), δ 32.4 (t), 37.5 (t), 38.7 (t), 44.0 (t), δ 46.1 (s), δ 47.8 (s), 6 48.2 (s), δ 51.6 (d), δ 63.4 (t), δ 107.9 (t), δ 155.9 (s). EIMS (70 eV) m/z: 220 [M]$^+$ (5), 189 (35), 187 (36), 163 (30), 161 (56), 160 (37), 159 (30), 147 (36), 145 (38), 133 (32), 131 (37), 119 (44), 107 (61), (91), 95 (94), 93 (57), 91 (100), 81 (53), 79 (60), 77 (52), 67 (39), 55 (45), 41 (62).

Amorpha-4,11-diene-12-ol was prepared from 100 mg artemisinic acid. The acid was dissolved in 6 mL of dry ether and esterified by adding diazomethane and mixing for 1 hour. GC-MS analyses of the reaction mixture showed the methyl ester and another compound (3:1), probably the methyl ester that was not connected to a cyclopropyl group. After removal of ether, 8.6 mg of the mixture was dissolved in 20 mL of ether-TBF (1:1) and cooled at −60° C. under a flow of dry nitrogen for 2 hours. The mixture was subsequently stirred for 1 hour at −30° C. with an excess of $LiAlH_4$, after which the reaction was stopped by the addition of $Na_2SO_4.10H_2O$. The temperature was raised to room temperature, and the reaction mixture was stirred an additional half hour. After drying with $MgSO_4$ overnight, the mixture was filtered through a Büchner funnel and the solvent removed. The desired alcohol was isolated and purified by preparative thin layer chromatography performed on silica gel plates, using a mixture of petroleum ether-ethyl acetate (3:1) as an eluent ($R_f$ 0.7). Amorpha-4,11-diene-12-ol was obtained in an overall yield of 14% as a mixture with 4-amorphene-12-ol (9:1). $^1$H NMR (400 MHz, $CDCl_3$): δ 0.87 (d, 3H, $Me_{15}$, J=6.0 Hz), δ 1.50 (br s, 3H, $Me_{14}$), δ 1.0–2.2 (m, 11H), δ 2.47 (m, 1H, $H_6$), δ 4.10 (s, 2H, $H_{12}$), δ 4.83 (br s, 1H, $H_{13'}$), δ 5.04 (br s, 1H, $H_{13}$), δ 5.18 (br s, 1H, $H_4$). EIMS (70 eV) m/z: 220 [M]$^+$ (6), 202 (35), 189 (66), 187 (34), 145 (40), 132 (52), 131 (36), 121 (100), 119 (81), 105 (51), 93 (74), 91 (70), 81 (47), 79 (77), 77 (50), 55 (41), 41 (47).

Extraction of the (+)-germacrene A Hydroxylase from Chicory Roots.

To prepare a crude enzyme extract that contains the cytochrome P450 enzymes including the (+)-germacrene A hydroxylase (de Kraker et al., 2001a), 25 grams of deep frozen (−80° C.) cubes of chicory roots were mixed by means of a Sorvall mixer together with 2.5 grams PVPP and 40 ml extraction buffer. During the whole procedure the plant material was kept on ice as much as possible. After 5 times several seconds of mixing, the slurry was transferred to the cheesecloth with an additional 10 ml of extraction buffer. The cheesecloth was squeezed out and the filtrate was centrifuged (Sigma 2K15) for 20 minutes at 20,000 g and 4° C. The supernatant was poured over a funnel filled with glass wool. The filtrate was divided over 8 ml centrifuge tubes and subsequently centrifuged (Centrikon T-2070, Kontron Instruments) for 90 minutes at 150,000 g and 4° C. The resulting microsomal pellets (about 6) were stored under argon at −80° C.

Before incubation, 10 pellets were pottered in 30 mL of assay buffer consisting of 25 mM Tris pH 7.5), 2 mM DTT, 1 mM ascorbic acid, 5 μM FAD, 5 μM FMN and 10% (v/v) glycerol. The enzyme suspension was divided in 1 mL aliquots and incubated with 5 μL substrate solution in the presence of a 1 mM NADPH-regenerating system that consisted of 1 mM NADPH, 5 mM glucose-6-phosphate, and 1.2 IU glucose-6-phosphate dehydrogenase (all from Sigma). The initial concentration of substrate in each assay was 45 µM and all were done in duplicate. To the blank assays no NADPH regenerating system was added, so that cytochrome P450 enzymes (including the (+)-germacrene A hydroxylase) were not active. After 60 minutes the incubations were stopped by storing them at −20° C. in a freezer.

The enzyme assays were extracted 2 times with 1 mL 20% (v/v) ether in pentane, after the addition of 5 µM cis-nerolidol (Fluka). The organic phase was filtered through a glasswool-plugged (dimethyl chlorosilane-treated, Chrompack) Pasteur pipette that contained 0.4 gram of silica and a little anhydrous $MgSO_4$. The pipette was rinsed with 1.5 mL ether and the extract was concentrated to approximately 50 µL under a stream of nitrogen. The concentrated extracts were analysed by GC-MS as described by De Kraker et al. (2001a).

To investigate whether enzymatic hydroxylations of the substrates were catalysed by the (+)-germacrene A hydroxylase, standard incubations of the various substrates (50 µM were carried out in the presence of 50 µM (+)-germacrene A, or 50 µM (−)-(α)-cubebene to exclude any possible general negative effect of sesquiterpene olefins on enzyme activity. To the control incubations 5 µL of ethanol was added, instead of the ethanol solution of either (+)-germacrene A or (−)-(α)-cubebene.

Results (Conversion of Tested Substrates)

Figure 6:
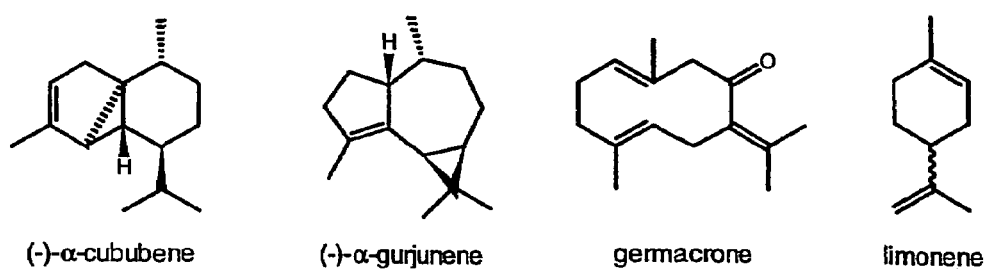
FIG. 6. Substrates that were not converted, i.e. (−)-(α)-cubebene, (−)-(α)-gurjunene, and germacrone; or hardly converted, i.e. limonene, by the (+)-germacrene A hydroxylase containing microsomal pellet from chicory roots.

Most of the tested substrates were hydroxylated (see Table 1) and their molecular mass was correspondingly raised with 16 amu. (−)-(α)-Cubebene and (−)-(α)-gurjunene which do not contain an isopropenyl or isopropylidene side chain were not converted (FIG. 6). Also germacrone was not accepted as a substrate. Some conversion of (+)-limonene and (−)-limonene occurred, but in such small amounts that it was not further investigated.

In Table I the sesquiterpenes are depicted that were converted into sesquiterpene alcohols in the presence of NADPH and the microsomal pellet that contains the (+)-germacrene A hydroxylase. The conversion rates of the various reactions are expressed relatively to the hydroxylation of β-selinene that is set at 100% and corresponds to a β-costol peak-size of 6.3× the internal standard (2.5 nmol cis-nerolidol in each assay). Approximately 30% of the added 50 nmol β-selinene was hydroxylated.Not all formed hydroxylation products could be identified, since reference samples or mass spectra of the expected sesquiterpene alcohols were not available.

Amorpha-4,11-diene

Incubation of amorpha-4,11-diene yielded two alcohols. The major product was identified as amorpha-4,11-diene-12-ol that results from hydroxylation of the isopropenyl side chain. The structure of the earlier eluting alcohol is unknown; though assuming an allylic hydroxylation that does not take place at a bridgehead atom, it is either amorpha-4,11-diene-2-ol or amorpha-4,11-diene-14-ol. EIMS (70 eV) m/z: 220 $M^+$(12), 189 (77), 162 (46), 147 (38), 121 (45), 119 (60), 107 (58), 105 (68), 95 (41) 93 (75), 91 (72), 81 (100), 79 (70), 77(48), 55 (52), 43 (49), 41 (52).

(−)-α-trans-Bergamotene

Incubation of (−)-α-trans-bergamotene yielded (E)-trans-bergamota-2,12-dien-14-ol, EIMS (70 eV) m/z: 220 $[M]^+$ (<1), 145 (10), 132 (28), 131 (10),121 (11), 120 (14), 119 (75), 107 (29), 105 (22), 95 (10), 94 (15), 93 (100),81 (14), 79 (33), 77 (31), 68 (17), 67 (11), 55 (29), 53 (11), 43 (36), 41 (28), 39 (14). Shaking the pentane-ether extract of the incubation with $MnO_2$ overnight yielded a compound that has the same retention time and mass spectrum as (E)-trans-bergamota-2,12-dien-14-al, present in costus root oil (Maurer and Grieder 1977).

(+)-γ-Gurjunene

Incubation of (+)-γ-gurjunene yielded an unknown sesquiterpene alcohol. EIMS (70 eV) m/z: 220 $[M]^+$ (35), 189 (36), 187 (37), 161 (39), 147 (31), 146 (35), 145 (55), 133 (33), 131 (64), 121 (41), 119 (54), 117 (31), 105 (81), 95 (41), 93 (58), 91 (100), 81 (92), 79 (71), 77 (54), 67 (38), 55 (49), 41 (59). Stirring the pentane-ether extract of the enzyme assay overnight with a spatula of $MnO_2$ gave complete conversion into an aldehyde or ketone ($[M^+]$218). Because this reagent is specific for α,β-unsaturated alcohols (March, 1992) and the only other available allylic position are at a tertiary carbon-atom, the biochemical hydroxylation must have occurred in the isopropenyl side chain of (+)-γ-gurjunene yielding 1S,4S,7R,10R)-5,11(13)-guaiadiene-12-ol.

(+)-Germacrene A (+)-Germacrene A was, according to previous results, converted into germacra-1(10),4,11-trien-12-ol, but somewhat unexpected the subsequent oxidations (approx. 15% of the produced germacrene alcohol) into germacra-1(10),4,11-trien-12-al and germacra-1(10),4,11-trien-12-oic were also clearly detected. This indicated that the microsomal pellet is not completely free of active dehydrogenases. Apparently the amount of produced germacrene alcohol is sufficient to enable these subsequent reactions. Moreover the dehydrogenases are active despite the used pH of 7.5 and the presence of the NADPH-regenerating system that reduces any $NADP^+$ present. In the incubations with β-selinene and β-elemene only minute quantities of aldehyde and/or acid were measured. For this reason the conversion of β-selinene was set at 100% and not that of (+)-germacrene A Germacrene B GC-MS analyses of the incubation of germacrene B yielded two products with an almost identical mass spectrum and retention time. Kovats' index 1694, EIMS (70 eV) m/z: 220 $[M]^+$ (<1), 202 (15), 187 (24), 159 (20), 147 (20), 145 (24), 134 (22), 131 (22), 123 (19), 121 (75), 120 (27), 119 (100), 109 (34), 108 (15), 107 (48), 106 (22), 105 (66), 95 (38), 94 (20), 93 (65), 92 (17), 91 (73), 81 (50), 79 (52), 77 (44), 71 (17), 69 (28), 68 (15), 67 (48), 65 (17), 57 (19), 55 (94), 53 (34), 43 (46), 41 (73), 39 (32). Kovats' index 1700, EIMS (70 eV) m/z: 220 $[M]^+$ (<1), 202 (15), 189 (15), 187 (21), 159 (20), 147 (22), 145 (23), 137 (17), 134 (21), 133 (28), 131 (26), 123 (22), 122 (15), 121 (100), 120 (28), 119 (91), 117 (15), 109 (36), 108 (18), 107 (52), 106 (23), 105 (77), 95 (45), 94 (24), 93 (86), 92 (21), 91 (80), 81 (61), 79 (66), 77 (53), 71 (21), 69 (32), 68 (18), 67 (55), 65 (21), 57 (32), 55 (69), 53 (43), 43 (62), 41 (91), 39 (42). Presumely both methyl groups in the isopropenyl side chain of germacrene B are hydroxylated yielding almost identical products. Hydroxylation at any other position is unlikely, because they would probably also have been observed for (+)-germacrene A The products are measured as their Cope-rearrangement products and lowering the injection port temperature from 250° C. to 150° C. yielded faint broadened peaks due to on-column Cope-rearrangement.

(+)-Ledene

Incubation of (+)-ledene yielded an unknown sesquiterpene alcohol. EIMS (70 eV) in/z: 220 $[M]^+$ (12), 187 (25), 159 (42), 151 (29), 147 (32), 145 (32), 133 (26), 131 (25), 121 (31), 119 (62), 107 (86), 105 (100), 95 (40), 93 (74), 91 (82), 81 (53), 79 (54), 77 (39), 55 (38), 43 (33), 41 (47).

Neointermedeol

Neointermedeol is presumably hydroxylated in the isopropenyl side chain like β-selinene, yielding 4β-H-eudesm-11(13)-ene,4,12-diol. EIMS (70 eV) m/z: 238 [M]$^+$ (<1), 223 (46), 135 (76), 93 (47), 81 (39), 79 (47), 71 (47), 55 (39), 43 (100), 41 (40).

Competitive Inhibition Experiments

The microsomal pellets that were used in the experiments do not exclusively contain the (+)-germacrene A hydroxylase, but also other membrane bound enzymes that are present in chicory roots. Hence, some of the conversion described in Table I might as well be catalysed by other oxidising enzymes than the (+)-germacrene A hydroxylase. To investigate this, incubations of the different substrates were done in the presence of 50 µM (+)-germacrene A. Incubations were also carried out with 50 µM (−)-α-cubebene instead, a sesquiterpene that is not hydroxylated (FIG. 6), to test the effect of the addition of any arbitrary sesquiterpene olefin on enzyme activity (see Table II).

The results presented in Table II show that all enzymatic hydroxylations were inhibited to 90% by the addition of (+)-germacrene A, except for β-selinene and neointermedeol whose hydroxylation was inhibited by 60 and 68%, respectively. The relatively small inhibition of β-costol formation agrees with the observation that it is nearly as well hydroxylated as (+)-germacrene A (Table I); the structural correlation between β-selinene and neointermedeol possibly also explains the small effect of (+)-germacrene A upon the formation of 4β-H-eudesm-11(13)-ene-4,12-diol. More surprisingly is that (+)-germacrene A also inhibits the formation of sesquiterpene alcohols in which no isopropenyl or isopropylidene side chain is involved, like ledene alcohol.

Hydroxylation of the sesquiterpenes is not dramatically influenced by the addition of (−)-α-cubebene, except for the formation of alloisolongifolene alcohol, a product that already under normal assay conditions is only formed in small quantities.

Effect on Enzyme Activity of Organic Solvents

Before experiments as described in this example were started, it was tested which organic solvent could be best used to dissolve the substrate. Stock solutions of 10 mM γ-gurjunene were prepared in hexane, pentane, iso-propanol ethanol and DMSO, and 5 µL of these solutions was added to the incubation-mixture. On the basis of the results of Table III ethanol was chosen as solvent for the substrates in all experiments, instead of the commonly used pentane (e.g. Karp et al., 1990).

Conclusions

A microsomal enzyme preparation from chicory roots can hydroxylate sesquiterpene olefins that are not present in chicory in the presence of NADPH (Table I). Most of these hydroxylations occur at the isopropenyl or isopropylidene side chain, yielding in some cases sesquiterpene alcohols that have not previously been described, e.g. amorpha-4,11-dien-12-ol and alloisolongifolene alcohol. The novelty of the formed sesquiterpene alcohols in some cases hampered their identification, and the structure assignment of the hydroxylation products of germacrene B, (+)-γ-guriunene and neointermedeol is tentative or, like for (+)-ledene, not possible at all. Unfortunately, these compounds were not yet produced in sufficient amount to isolate them for structure elucidation by $^1$H NMR. The substrates for hydroxylation preferably do not contain any polar group, according the observation that neointermedeol is 15-fold less efficiently hydroxylated than β-selinene and the observation that germacrone is not hydroxylated whereas germacrene B is. The size of the substrate is also of importance as bydroxylation of limonene, a smaller monoterpene, did hardly occur. In the case of amorpha-4,11-diene two distinct sesquiterpene alcohol products were formed.

Hydroxylations occurring at isopropenyl side chains and—less efficiently—at isopropylidene side chains are catalysed by the (+)-germacrene A hydroxylase that is present in the microsomal pellet of chicory roots. Accordingly, these hydroxylations could be competitively inhibited by (+)-germacrene A (Table II). Hydroxylations of various non-natural substrates by a cytochrome P450 enzyme of plant secondary metabolism contradicts the common belief that enzymes of plant secondary metabolism have a narrow substrate specificity. (Donaldson and Luster, 1991; Halkier, 1996; Schuler, 1996; Mihaliak et al., 1993; Karp et al., 1990).

Formation of the unknown ledene alcohol and the unknown amorpha-4,11-diene alcohol (KI 1720) cannot have occurred in an isopropenyl/isopropylidene side chain, nevertheless these reactions are also inhibited by (+)-germacrene A. Although hard to understand, it suggests the involvement of the (+)-germacrene A hydroxylase in these reaction as well. Notably, the rate of competitive inhibition by (+)-germacrene A of the formation of amorpha-4,11-diene-12-ol and the unknown amorpha-4,11-diene alcohol is the same.

The hydroxylation of amorphadiene-4,11-diene in the isopropenyl side chain is interesting as well. It was hypothesised to be an important step in the formation of the anti-malarial drug artemisinin in *Artemisia annua* but has not yet been reported for this plant (Bouwmeester et al., 1999a).

Figure 7:
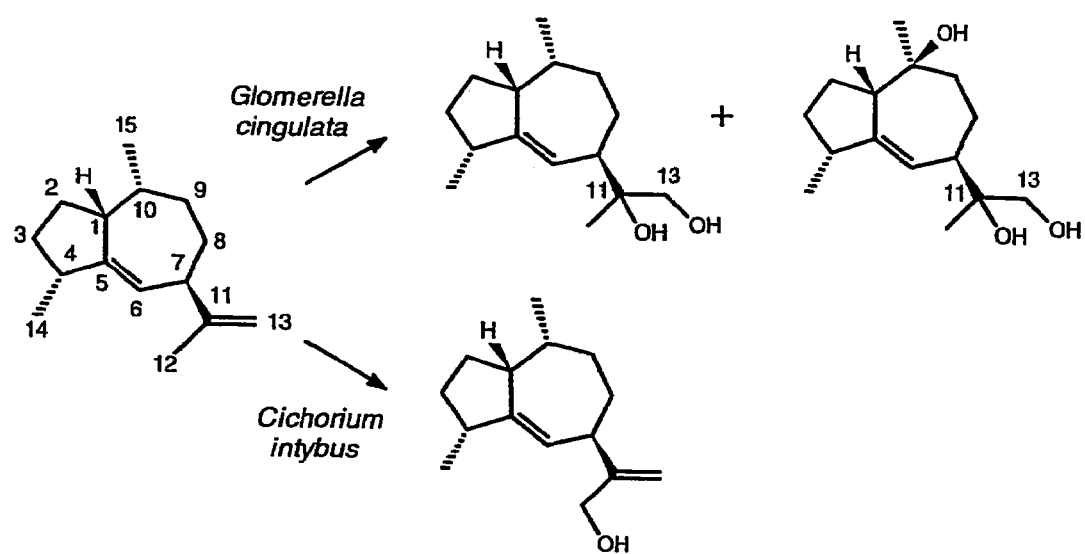
FIG. 7. Biotransformation of (+)-γ-gurjunene with a plant pathogenic fungus yields (1S,4S, 7R, 1OR)-5-guaien-11,13-diol and (1S,4S,7R, 10S)-5-guaien-10,11,13-triol; incubation of γ-gurjunene with a microsomal pellet of chicory gave (1S,4S,7R, 1R)-5,11(13)-guaiadiene-12-ol.

Generally, the production of new materials for the flavor and fragrance industry has been a powerful driving force in the research on the hydroxylation of terpenes by microorganisms. Although in some cases successful, these microbiological conversions often yield a broad spectrum of products, including epoxides and diols (Lamare and Furstoss, 1990; Drauz and Waldmann, 1995; Faber, 2000) and the oxidations often occur at double bonds. In contrast, the hydroxylations catalysed by the microsomal pellet of chicory yield one, sometimes two products, and occur more regiospecifically. Illustrative is the case of (+)-γ-gurjunene: incubation with the plant pathogenic fungus *Glomerella cingulata* yields (1S,4S,7R,10R)-5-guaien-11,13-diol and (1S,4S,7R,10S)-5-guaien-10,11,13-triol (Miyazawa et al., 1998), whereas incubation with the microsomal pellet of chicory yielded (1S,4S,7R,10R)-5,11(13)-guaiadien-12-ol (FIG. 7).

EXAMPLE 2

Figure 2:
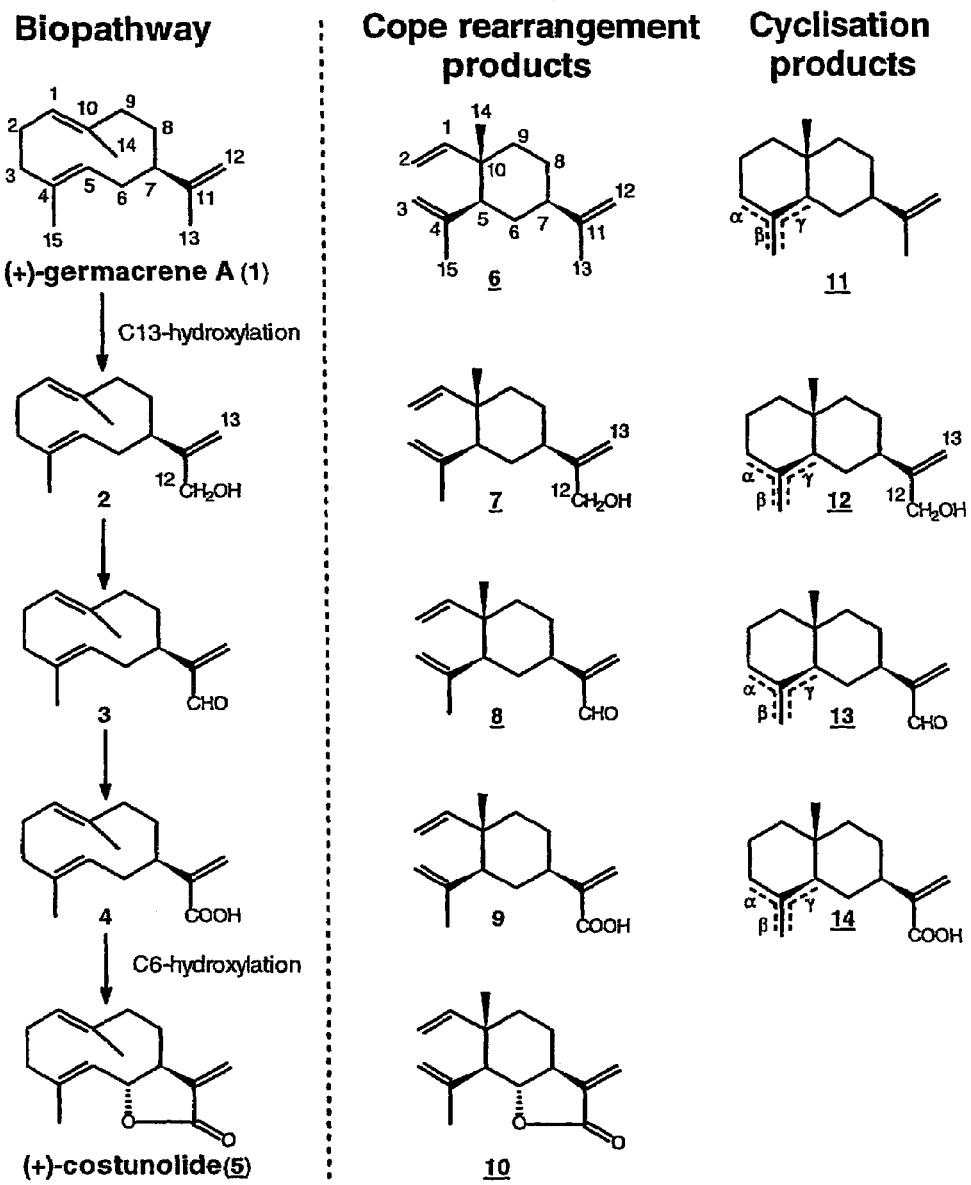
FIG. 2. Proposed biosynthetic route from (+)-germacrene A (1) to (+)-costunolide (5) via germacra-1(10),4,11(13)-trien-12-ol (2), germacra-1(10),4,11(13)-trien-12-al (3), and germacra-1(10),4,11(13)-trien-12-oic acid (4). At the right side of the dotted line, compounds are shown that can be formed from these unstable germacrenes: the heat induced Cope rearrangement products (−)-β-elemene (6), (−)-elema-1,3,11(13)-trien-12-ol (7), (−)-elema-1,3,11(13)-trien-12-al (8), elema-1,3,11(13)-trien-12-oic acid (9), and dehydrosaussurea lactone (10); and the acid induced cyclisation products selinene (11) (γ-selinene is usually named selina-4,11-diene), costol (12), costal (13), and costic acid (14). Compounds with underlined numbers have all been identified in costus roots; (+)-germacrene A (1) and germacra-1(10),4,11(13)-trien-12-al (3) were isolated from other plant species. Note that after hydroxylation the numbering of carbon atoms 12 and 13 is inverted.
Figure 8:
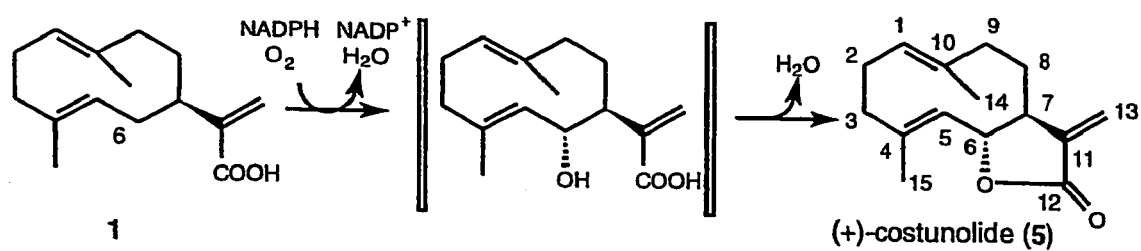
FIG. 8. Postulated cytochrome P450 catalysed conversion of germacra-1(10),4,11(13)-trien-12-oic acid(4) into (+)-costunolide (5) via hydroxylation and subsequent lactonisation.

Identification and Characterisation of Enzymes Involved in the Conversion of Germacrene Acid to Sesquiterpene Lactones (+)-Costunolide is the most rudimentary structure of a germacranolide and considered to be the parent-compound of all germacrene-derived sesquiterpene lactones, among them the guaianolides, eudesmanolides and germacranolides of chicory. It is very likely that this compound is formed from FPP through (+)-germacrene A, germacra-1(10),4,11 (13)-trien-12-ol, and germacra-1(10),4,11(13)-trien-12-oic acid (4) (FIG. 2) (De Kraker et al., 1998, 2001a). This germacrane acid 4 is thought to be hydroxylated at the $C_6$-position by a cytochrome P450 enzyme after which lactonisation yields (+)-costunolide (5) (FIG. 8) Germacrene acid was isolated from fresh costus roots (De Kraker et al., 2001b), which makes it possible to investigate this last step in formation of the lactone ring of sesquiterpene lactones (Geissman, 1973; Fischer et al., 1979; Fischer, 1990).

(+)-Costunolide is considered to be a branching point in the biosynthesis of sesquiterpene lactones from where pathways for the formation of guaianolides, eudlesmanolides and germ acranolides divides It has been postulated by various authors that cyclisation of (+)-costunolide to either guaanolides or eudesmanolides is mediated by respectively $C_4$–$C_5$ epoxidation or $C_1$–$C_{10}$ epoxidation, respectively (Brown et al., 1975; Fischer 1990; Teisseire, 1994; Piet et al., 1995). Alternatively, the necessity of a $C_3$-hydroxylation of the germacrenolide for formation of a guaianolide has been proposed (Piet et al., 1996).

Materials and Methods

Figure 9:
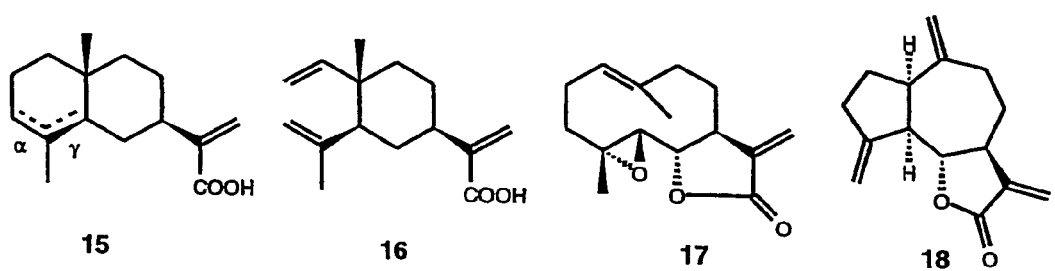
FIG. 9. Various substrates that were also incubated with the chicory supernatant and NADPH: a mixture of α- and γ-costic acid (15), elema-1,3,11(13)-trien-12-oic acid (16), parthenolide (17) and dehydrocostus lactone (18).

Fresh roots of cultivated chicory (Cichorium intybus L., cv Focus) were harvested during late summer and obtained from a grower (J. de Mik) in Veenendaal, the Netherlands. The chicory roots were cut into small pieces, frozen in liquid nitrogen and stored at –80° C. Germacra-1(10),4,11(13)-trien-12-oic acid (4), (+)-costunolide (5), and dehydrocostus lactone (FIG. 9, 18) were isolated from costus roots (D)e Kraker et al., 2001b). Synthesis of a mixture of α- and γ-costic acid is described by De Kraker et al. (2001b), whereas the synthesis of elema-1,3,11(13)-trien-12-oic acid (9) is described in (de Kraker et al., 2001a). A sample of leucodin (22) was kindly provided both by Prof. M. Ando (Niigata University, Japan; Ando et, al., 1994) and Dr. Shi Yong Ryu (Korea Research Institute of Chemical Technology, Yusung, Taej on, Korea), who also provided its $C_{11}$-epimer achillin (Ho et al., 1998). 11,13-Dihydro-dehydrocostus lactone (mokko lactone) was a gift of Prof. Y. Asakawa C(okushima Bunri University, Japan). Parthenolide (17) was purchased from Sigma, cis-nerolidol from Fluka. Ether (diethyl ether) and pentane were redistilled before use.

A GC-standard of 11(S),13-dihydro-costunolide (20) was prepared from 2 mg of (+)-costunolide (5) that was dissolved in 1.5 mL ethyl acetate and stirred with 1.5 mg of NaBH$_4$ at 0° C., a procedure described for the reduction of the $C_{11}$–$C_{13}$ exocyclic double bond of various sesquiterpene lactones (Asakawa et al., 1980; Asakawa, 1982; Seto et al., 1988). After 45 minutes the reaction was stopped by the addition of 1% HAc and 2 ml extra ethyl acetate. The organic phase was filtered through a glass-wool plugged Pasteur pipette that contained 0.45 g of silica and a little anhydrous MgSO$_4$. GC-MS analysis of the filtrate showed that half of the (+)-costunolide was converted into 11(S), 13-dihydro-costunolide, whereas no trace of its $C_{11}$-epimer was detected.

Enzyme Isolation and Assay for (+)-Costunolide Synthase Activity

A cell free extract of chicory roots was prepared from the frozen material in the same way as described for isolation of the germacrene A hydroxylase (Example 1), but MgCl$_2$ was not added to the extraction buffer since the accompanying (+)-germacrene A synthase activity was not essential for the detection of (+)-costunolide synthase activity. The prepared 20,000 g supernatant was desalted with an Econo-Pac 10 DG column (Biorad) to an assay buffer consisting of 25 mM Tris (pH 7.5), 1 mM ascorbic acid, 5 μM FAD 5 μM FMN and 10 %(v/v) glycerol. DTT was omitted from the assay buffer, because SH-groups present in DTT might undergo an "Michael-type addition" to the $C_{11}$–$C_{13}$ exocyclic double bond of (+)-costunolide Kupchan et al., 1970). A 1-ml aliquot of the desalted supernatant was incubated with 3 μL of a 15 mM solution of germacrene acid (4) in tert-butyl-methylether and a 1 mM NADPH-regenerating system, which consists of 1 mM NADPH, 5 mM glucose-6-phosphate, and 1.2 IU glucose-6-phosphate dehydrogenase (all from Sigma). Incubations were also done with boiled desalted supernatant and in the absence of NADPH. The experiments were repeated with elema-1,3,11(13)-trien-12-oic acid (FIG. 2, 9) and a mixture of α- and γ-costic acid (14) that might serve as substrate analogues for the germacrene acid (4). After 1 h of incubation at 30° C., the reactions were stored in the freezer.

The incubations were extracted three times with 1 mL of 20% (v/v) ether in pentane, after the addition of a 0.2 mM cis-nerolidol solution in ethanol that serves as internal standard. The organic phase was filtered through a glass-wool plugged (dimethyl chlorosilane-treated glasswool; Chrompack) Pasteur pipette that contained 0.45 g of silica and a little anhydrous MgSO$_4$. The column was washed with 1.5 ml of ether and the extract was carefully concentrated to approximately 50 μL under a stream of nitrogen. Samples of 2 μL were analysed by GC-MS using an injection port temperature of 320° C. to provoke Cope rearrangement of (+)-costunolide (5). Mass spectra were recorded at 70 eV scanning from 35 to 300 atomic mass units; the GC oven temperature was programmed as described before (de Kraker et al., 1998).

Characterisation of (+)-Costunolide Synthase Activity

To determine whether the formation of (+)-costunolide (5) from germacrene acid (4) was catalysed by a cytochrome P450-enzyme, the effect of various established cytochrome P450-inhibitors (cytochrome C, metyrapone, clotrimazole, micozanole, and amino-benzotriazole) on this reaction were tested, as well as the effect of CO or an argon atmosphere. The cofactor dependence was also investigated, i.e. NAD (P)$^+$ or NADH was added instead of NADPH. Experiments were carried out in a similar manner as described for the germacrene A hydroxylase in Example I using a 20,000 g supernatant and 5 μL of 0.2 mM cis-nerolidol as internal standard. Blue-light reversal of CO-inhibition was investigated with gas-mixtures of 10% O$_2$ plus 90% N$_2$ (blank) and 10% O$_2$ plus 90% CO.

Incorporation of oxygen was investigated with $^{18}O_2$ (99% pure; Icon Services, Mt. Marlon, N.Y., USA). One ml of incubation mixture, placed in a (vented) septum-capped 4.5-mL vial, was first bubbled with nitrogen to remove air and next with oxygen-18. The mass spectra of the formed compounds were compared with those formed in the standard enzyme assays with air.

Investigation of Subsequent Conversions of (+)-Costunolide

Incubations as described for the germacrene acid were also done with (+)-costunolide (30 μM) to test whether any further enzymatic conversion of this compound would occur during the incubation of germacrene acid. Parthenolide (20 μM) (FIG. 9, 17) was incubated as well since it might be an intermediate in the formation of guaianolides. Dehydrocostus lactone (20 μM) (18) was incubated as a model compound for reductions that occurred at the $C_{11}$–$C_{13}$ exocyclic double bond of (+)-costunolide. The effect of established cytochrome P450 inhibitors and CO on the conversion of (+)-costunolide was studied, just as the effect of various pyridine nucleotide cofactors and an argon atmosphere.

Conversion of Germacrene Acid into Sesquiterpene Lactones

Figure 3:
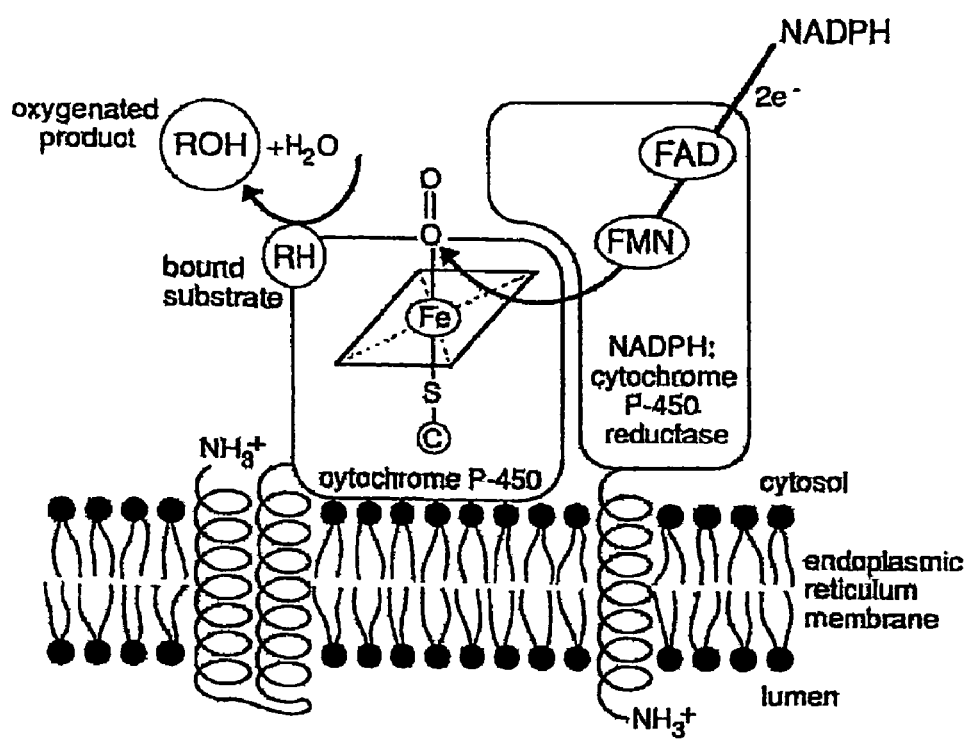
FIG. 3. Schematic drawing of the cytochrome P450 complex (taken from Meijer, 1993). Instead of $O_2$, cytochrome P450 is also able to bind CO which inhibits its catalytic action.
Figure 4:
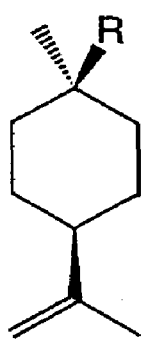
FIG. 4. Chemical structure of α- and β-terpineol and their acetate esters.
Figure 4:
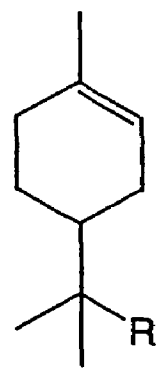
Figure 5:
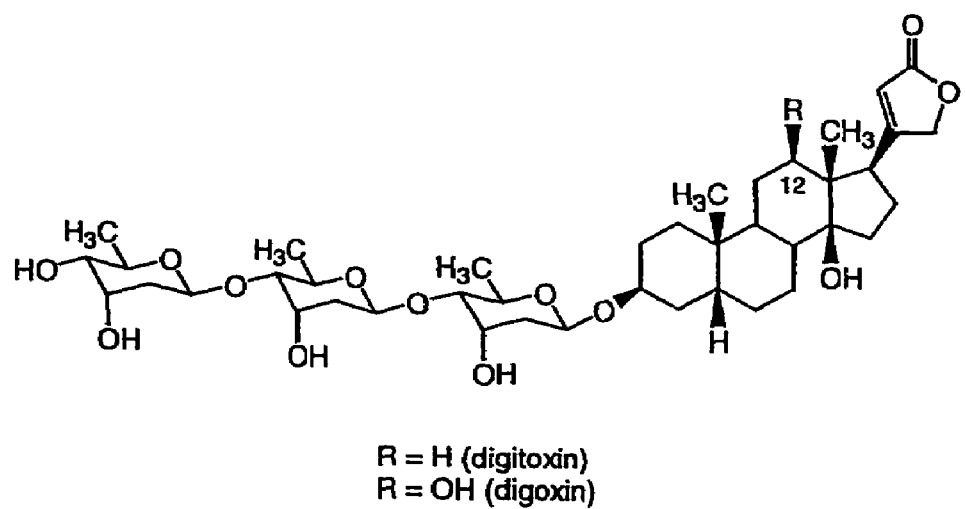
FIG. 5. Chemical structure of digitoxin and digoxin.
Figure 10:
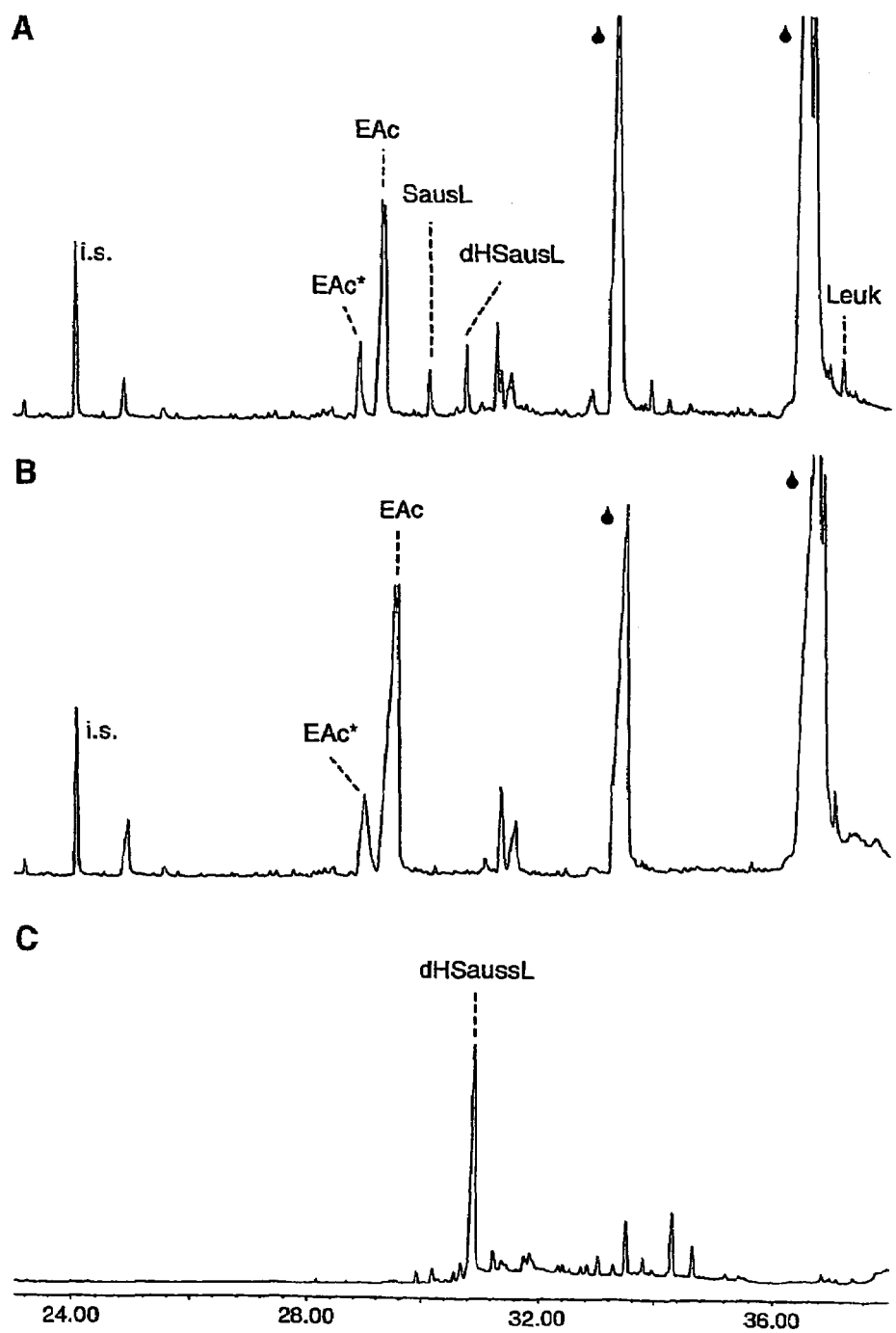
FIG. 10. A, GC-MS analyses of the products formed in the incubation of a 20,000 g supernatant from chicory roots with NADPH and germacra-1(10),4,11(13)-trien-12-oic acid (4) displays peaks of dehydrosaussurea lactone (dHSausL [7]), saussurea lactone (SausL [9]), and leukodin (Leuk [10]). B, These products are not observed in the absence of NADPH. Germacrene-1(10),4,11(13)-trien-12-oic acid (1) is observed as elema-1,3,11(13)-trien-12-oic acid (EAc) plus its diastereomer (EAc*); the internal standard (i.s.) is 1 nmol cis-nerolidol. The huge fronting peaks (●) are fatty acids (palmatic- and linoleic acid). C, A standard of 0.5 mM costunolide (2) in ethanol yields a tailing peak of dehydrosaussurea lactone (dHSausL [7]).

GC-MS analyses of the pentane-ether extract from the incubation of a 20,000 g chicory root supernatant with germacra-1(10),4,11(13)-trien-12-oic acid (4) in the presence of an NADPH-regenerating system showed three products that were not detected in incubations without NADPH or in incubations with boiled supernatant (FIG. 10 A+B): The major peak co-eluted with a standard of (+)-costunolide (5) that at an injection-port temperature of 320° C. is detected as its Cope-rearrangement product dehydrosaussurea lactone (10) (FIG. 3C). The substrate germacrene acid was also measured as it Cope-rearrangement product(s), i.e. elemene acid (9) and diastereomeric elemene acid (de Kraker et al., 2001b).

Figure 11:
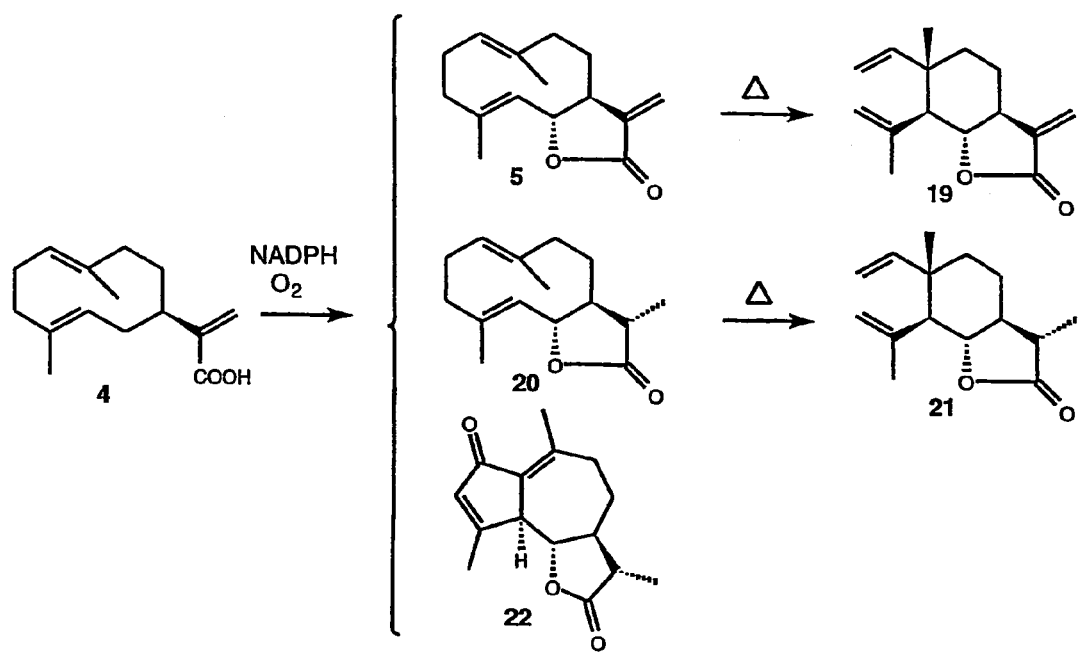
FIG. 11. Products formed from germacra-1(10),4,11(13)-trien-12-oic acid (4) in the presence of NADPH and oxygen by a chicory 20,000g supernatant. Leukodin (22) is detected as a genuine GC-peak, whereas costunolide (5) and 11,13-dihydrocostunolide (20) are detected as their Cope-rearrangement products dehydrosaussurrea lactone (19) and saussurea lactone (21), respectively.

The two other products were identified as 11(S), 13-dihydrocostunolide (20) that is Cope-rearranged into saussurea lactone (21), and leucodin (22) (FIG. 11). Both 11(S) .13-dihydrocostunolide and leucodin are enzymatically formed from (+)-costunolide and accordingly they also appeared in incubations of (+)-costunolide with the 20,000 g supernatant and NADPH. It cannot be excluded that even more products are formed during the incubation of germacrene acid, because higher oxygenated sesquiterpene lactones are likely not volatile enough for detection by gas chromatography. Furthermore, the presence of fatty acids in chicory extracts (Sannai et al., 1982) complicates the GC-analysis, because they yield big peaks (●) under which smaller product peaks might "disappear".

There was no detectable conversion of the substrate analogues α- and γ-costic acid (14) and elema-1,3,11(13)-trien-12-oic acid (9).

Characterisation of the (+)-Costunolide Synthase

For characterisation of the (+)-costunolide synthase the response of the GC-MS to different concentrations of (+)-costunolide should preferably be linear. Yet, at the used injection port temperature of 320° C., the GC-trace of costunolide (FIG. 10C) does not show a sharp peak of dehydrosaussurea lactone (19)—but a tailing peak that contains minor peaks of costunolide-related products like α- and β-cyclocostunolide. Apparently (+)-costunolide is more resistant to Cope-rearrangement than for instance germacrene acid (4). In literature it has also been noticed that a lactone ring has a strong influence on the thermal stability of germacrenes, and that Cope-rearrangement of (+)-costunolide is reversible (Jain et al., 1970; Minnaard, 1997). Therefore, on a GC-column dehydrosaussurea lactone (19) might even undergo to some extent the reverse reaction towards (+)-costunolide (Grieco and Nishazwa, 1977). Avoiding Cope-rearrangement in the injection port by lowering the injection port temperature would nevertheless result in Cope-rearrangement of (+)-costunolide during its migration through the column and yielded a broad hump (similar to the one shown for germacrene aldehyde in Example 1) instead of a clear (+)-costunolide peak. Despite the poor quality of the dehydrosaussurea lactone GC-peak, it is linear with injected (+)-costunolide concentrations in the range of 5 μM to 50 μM. The response factor relative to cis-nerolidol is 0.15, and concentrations below 5 μM are not measurable which means that (+)-costunolide concentrations below 0.25 μM in the incubation mixture, i.e. 0.25 nmol, are not detected.

More of a problem for characterisation of the (+)-costunolide synthase is that almost certainly not all subsequent conversion products of costunolide are detected. Hence, the given enzyme activities are a summation of the peaks of dehydrosaussurea lactone (19), saussurea lactone (21) and leucodin (22) and are consequently more an indication than an absolute value of costunolide synthase activity. Quantitative measurement of the elemene acid peak (substrate peak) was not an option, because it is not linear with concentration and, more generally, acid peaks on GC are of poor quality.

Table IV shows that the costunolide synthase is dependent on oxygen and NADPH, whereas NADH was much less effective as a reductant. This suggests the involvement of a cytochrome P450 enzyme, which was confirmed by the effect of various established cytochrome P450 inhibitors (West, 1980; Mihaliak et al., 1993). In the presence of cytochrome C (100 μM), no enzymatic products of germacrene acid (4) were measured; miconazole (100 μM) reduced the amount of measurable products with 71%, aminobenzotriazole (100 μM) with 44%, metyrapone (1 mM) with 78%, and clotrimazole (100 μM) with 97%.

Figure 12:
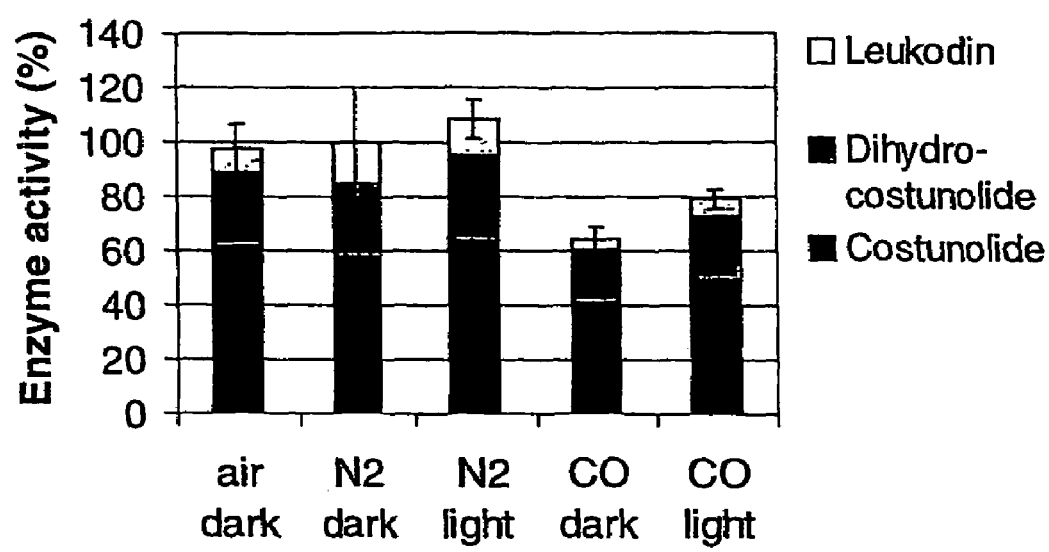
FIG. 12. Demonstration of blue light reversible CO-inhibition of the costunolide synthase. Enzyme activity in the presence of 90% $N_2$+10 $O_2$ (N2) is set at 100% and this activity corresponds to a peak of dehydrosaussurea lactone (costunolide), saussurea lactone (dihydrocostunolide) and leucodin of respectively 0.58, 0.27, and 0.15×internal standard (1 μM). The inhibition in the presence of 90% CO+10% $O_2$ was slightly reversed by irradiation with blue light (450 nm). All incubations were done in the absence of FAD and FMN.

The strongest proof for the involvement of a cytochrome P450 enzyme is blue-light reversible inhibition of enzyme activity by CO (West 1980; Mihaliak et al., 1993). The results depicted in FIG. 12 show an inhibitory effect of CO on the produced sum of (+)-costunolide, 11(S),13-dihydrocostunolide and leucodin that could be reversed by blue light, to some extent.

Characterisation of the Subsequent Conversions of (+)-Costunolide

Incubation of (+)-costunolide with a 20,000 g supernatant chicory root supernatant in the presence of NADPH yielded 11(S),13-dihydrocostunolide (20) and leucodin (22). No other products were detected upon GC-MS analyses of the incubation, but comparison of the decrease in peak height of dehydrosaussurea lactone with the intensity of the products peaks products strongly suggested the formation of other products that are not detected on GC. The enzyme activity that catalyses the reduction of the 11(S), 13-exocyclic double bond of costunolide was not capable of doing the same with dehydrocostus lactone (18). Incubation of parthenblide (17) did not give leucodin (22), but conversion of parthenolide into other not-measurable sesquiterpene lactones cannot be excluded. Parthenolide itself disintegrates upon GC-analyses in a number of peaks and hence no quantitative determination was done on the amount of parthenolide present in after incubation.

To test which type(s) of enzymes might catalyse the formation of 11(S),13-dihydrocostunolide (20) and leucodin (22) the pyridine nucleotide cofactors were varied (Table V). Formation of both compounds is dependent upon NADPH, but a part of the (+)-costunolide reductase activity is retained in the absence of any cofactor.

Table VI shows that formation of leucodin from (+)-costunolide is dependent upon oxygen, whereas the formation of 11,13-dihydrocostunolide is not. Formation of leucodin is strongly inhibited by CO which suggests the involvemenit of a cytochrome P450 enzyme. Accordingly it is also inhibited by all of the tested cytochrome P450 inhibitors except amino-benzotriazole.

Incorporation of Oxygen-18

Figure 13:
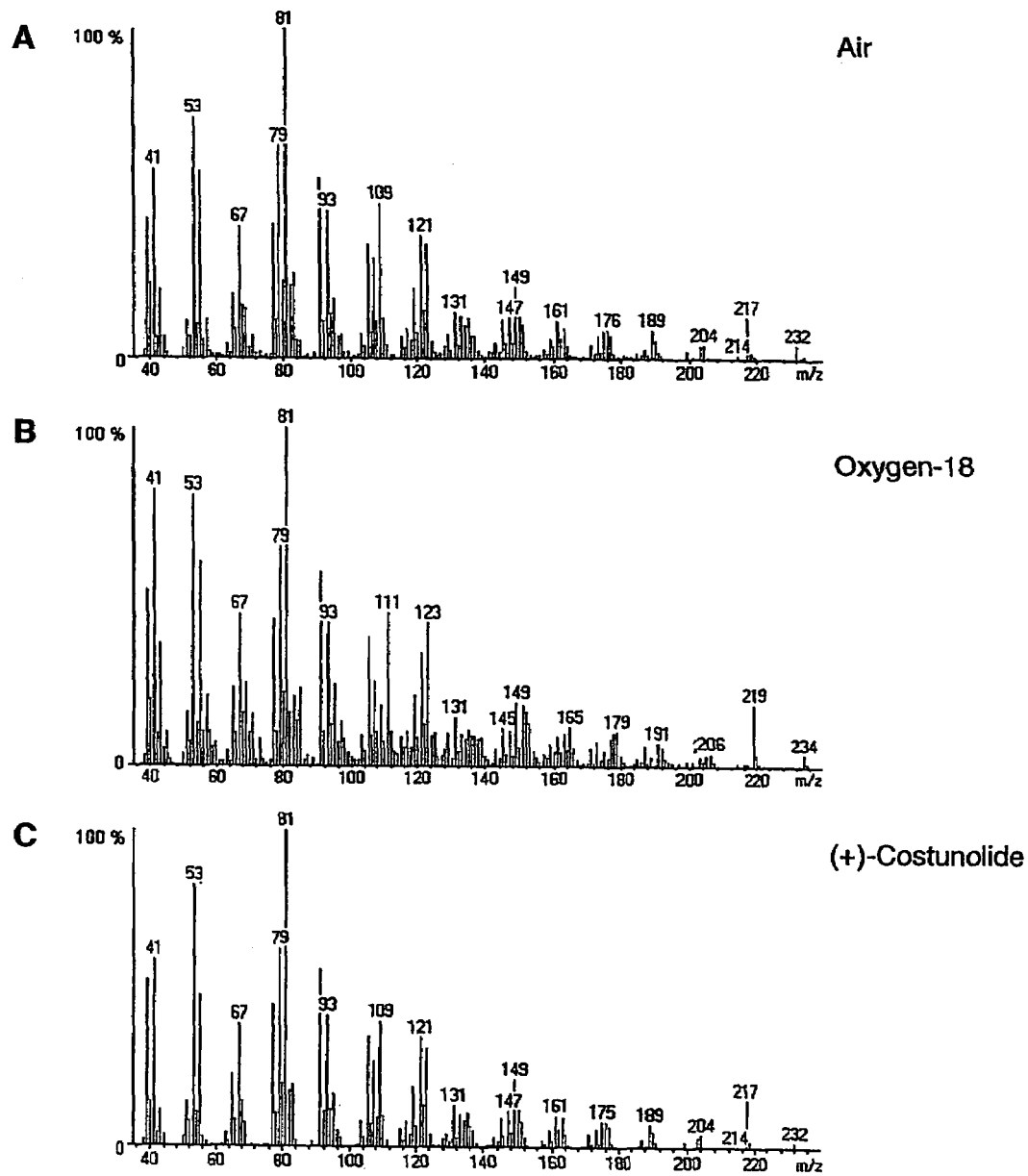
FIG. 13. Mass spectra of dehydrosaussurea lactone (19) originating from (+)-costunolide (5) that has been produced from germacrene acid (4) under standard assay conditions (A), in the presence of $^{18}O_2$ (B), or that originates from a standard of (+)-costunolide (C).

Incubation of germacrene acid (4) in the presence oxygen-18 gave the incorporation of one atom of $^{18}O$ into (+)-costunolide (5). The molecular ion peak in the mass spectrum of dehydrosaussurea lactone (19) was raised from 232 to 234 amu (FIG. 13). Similar changes were observed in the mass spectrum of saussurea lactone (21), the Cope rearrangement product of 11(S),13-dihydrocostunolide (20). Its ion peak was shifted from 234 to 236 amu whereas the [M-Me]$^+$ peak was shifted from 219 to 222 amu. Bubbling of the enzyme assay with oxygen-18 (99%) had not any measurable negative effect on enzyme activity.

Figure 14:
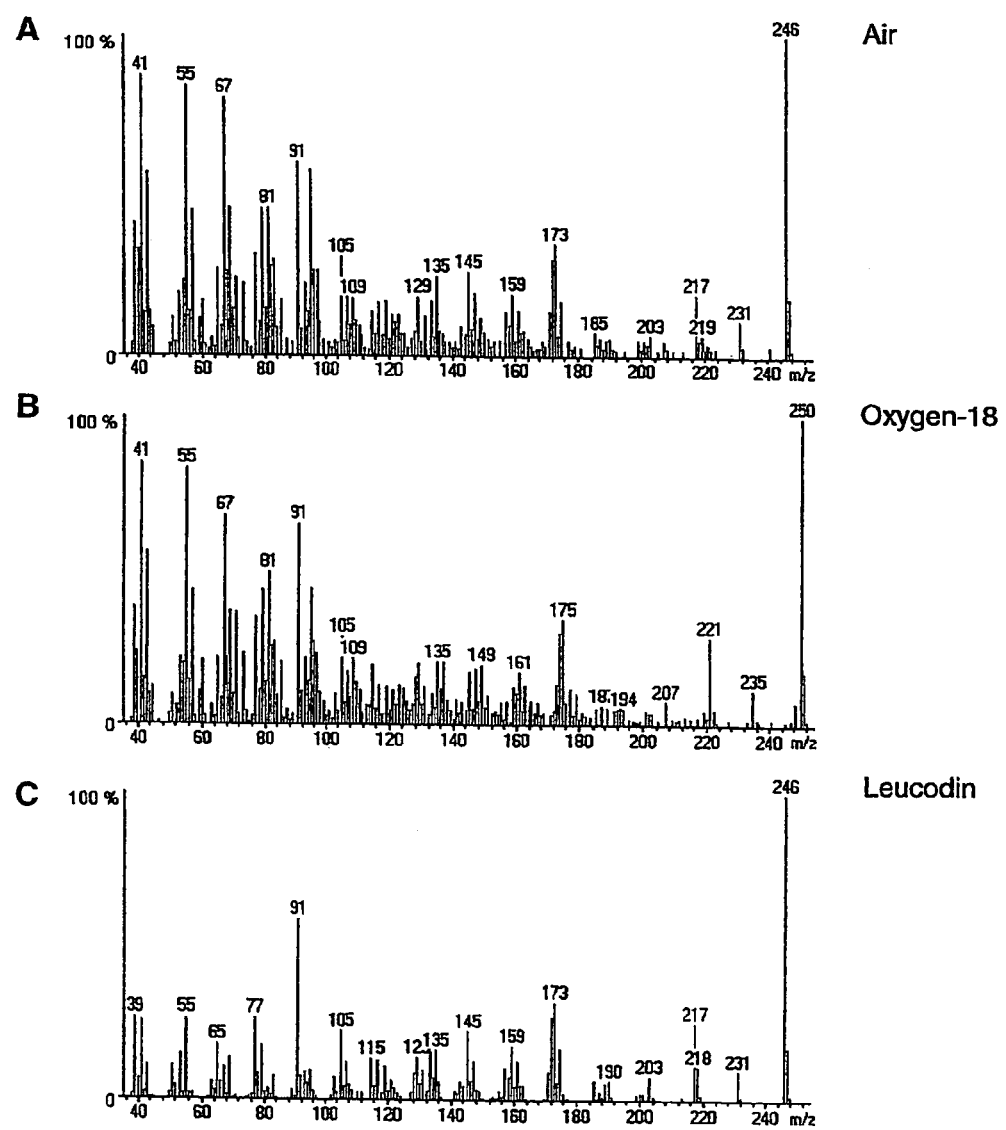
FIG. 14. Mass spectra of leucodin (22) produced from germacrene acid (4) in an enzyme assay under standard conditions (A) or in the presence of $^{18}O_2$ (B). Panel C shows the mass spectrum of the leucodin standard (C).

The mass spectra of leucodin showed the incorporation of two atoms of $^{18}O$ and the mass of the ion peak was clearly raised with 4 units from 246 to 250 amu (FIG. 14). Unfortunately, in the enzyme assay the GC-peak of leucodin is superpositioned on the tailing peak of linoleic acid (FIG. 10A) which contaminates the mass spectrum of leucodin particular in the lower mass range.

Conclusions

The present results show that chicory contains an enzyme that converts germacra-1(10),4,11(13)-trien-12-oic acid (4) into (+)-costunolide (5), yielding the lactone ring present in sesquiterpene lactones. This step is the final proof for the postulated pathway from FPP through (+)-germacrene A, germacra-1(10),4,11(13)-trien-$^{12}$-ol, and germacra-1(10),4,11(13)-trien-12-oic acid (4) to the germacrene-derived sesquiterpene lactones (Geissman, 1973; Fischer et al., 1979; Fischer, 1990).

Figure 15:
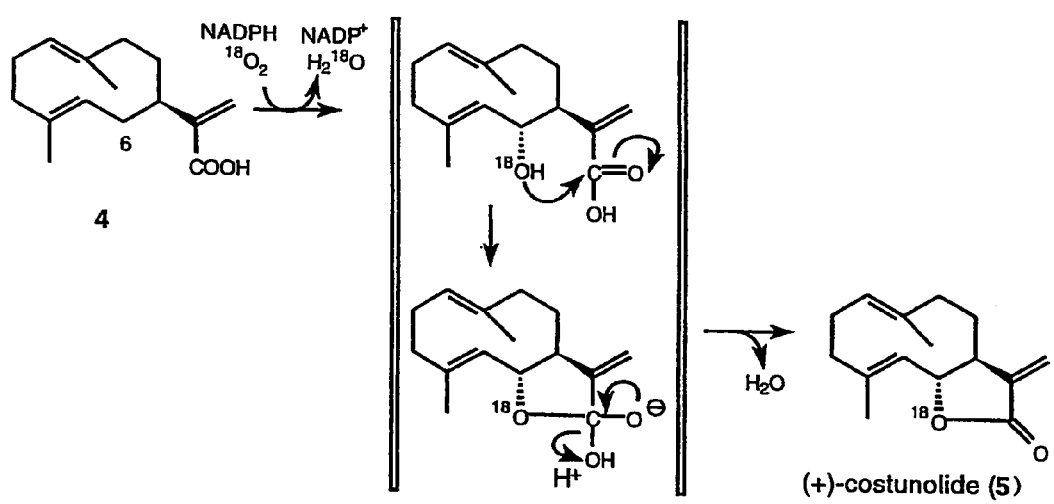
FIG. 15. Mechanism for the enzyme catalysed formation of (+)-costunolide (5) from germacrene acid (4) that results in the incorporation of one atom of $^{18}O$.

The (+)-costunolide synthase is a cytochrome P450 enzyme that is dependent upon NADPH and $O_2$ and is accordingly inhibited by various established cytochrome P450 inhibitors (West, 1980; Mihaliak et al., 1993). Blue light reversible CO-inhibition of enzyme activity could be demonstrated as well, although the results were somewhat disturbed by subsequent enzymatic conversions of (+)-costunolide. Incubation in the presence of oxygen-18 showed the incorporation of one atom of $^{18}O$ into (+)-costunolide, another typical feature of cytochrome P-450 enzymes (West, 1980; Mihaliak et al., 1993). It also confirms the mechanism in which germacrene acid is first hydroxylated at the $C_6$-position (Fischer et al., 1979) after which this hydroxyl group attacks, presumably enzyme-mediated, the carboxyl group at $C_{12}$. During the resulting lactonisation it so happens that the oxygen isotope is incorporated in the lactone ring (FIG. 15).

The (+)-costunolide synthase is not capable of converting the substrate analogues α-costic acid (FIG. 2, 14), or elema-1,3,11(13)-trien-12-oic acid (9) which is not unexpected, because the $C_6$-position is not allylic. However, γ-costic acid (13), in which the $C_6$-position is allylic, was not converted either, so apparently the geometry of the cyclodecadiene ring system is necessary for reaction.

Figure 16:
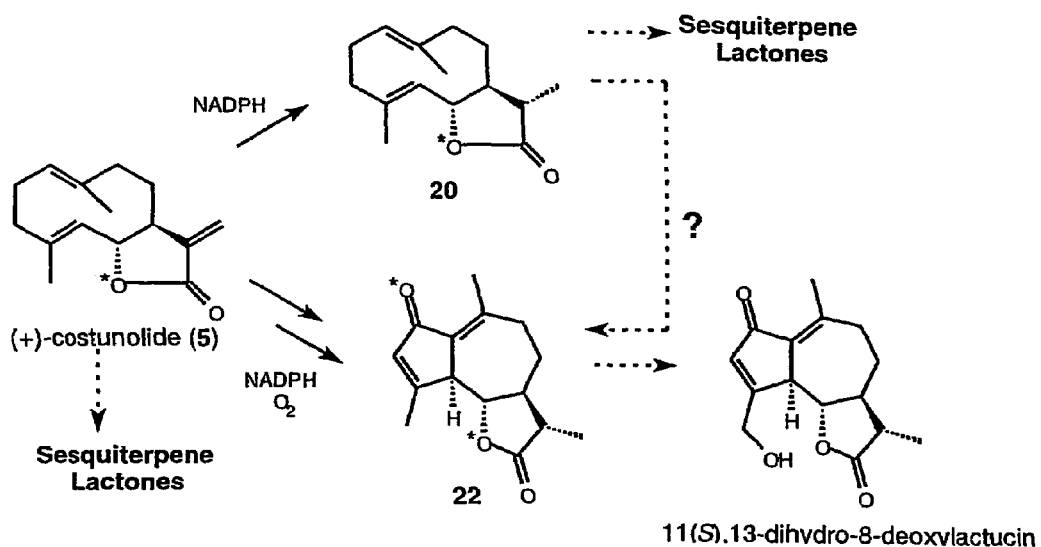
FIG. 16. (+)-Costunolide (5) is in the presence of NADP and $O_2$ further enzymatically converted into 11(S),13-dihydrocostunolide (20) and leucodin (22). Incubation of germacrene acid in the presence of $^{18}O_2$ gives incorporation at positions marked with an asterisk. It is unclear whether leucodin (22) is formed via 20. Both (+)-costunolide and 11(S), 13-dihlydrocostunolide (20) are likely precursors of other sesquiterpene lactones present in chicory; whereas leucodin (22) is only one hydroxylation away from 11(S), 13-dihydro-8-deoxylactucin, a minor sesquiterpene lactone of chicory.

(+)-Costunolide (5) is in incubations with NADPH and the 20,000 g supernatant of chicory roots subsequently converted into 11(S),13-dihydrocostunolide (20) and leucodin (22) (FIG. 16). Formation of 11(S),13-dihydrocostunolide is not dependent upon oxygen, but is strongly enhanced in the presence of NADPH whereas a small enzyme activity of 15% is retained in its absence. The reduction of the $C_{11}$–$C_{13}$ exocyclic double bond issimilar to the type of reactions catalysed by enoate reductases, a group of iron-sulphur flavoproteins that has been isolated from *Clostridium* and catalyses the reduction of the olefinic bond of α,β-unsaturated carboxylic acids under anaerobic conditions in the presence of reducing agents (Holland, 1992). The reduction of the $C_{11}$–$C_{13}$ exocyclic double bond in costunolide occurs stereoselectively and yields only the 11(S), 13-stereoisomer is formed. The stereochemistry at C11 is identical to that of the 11(S),13-dihydro sesquiterpene lactones present in chicory (Seto et al., 1988; van Beek et al., 1990).In contrast to chicory, some other plant species contain $C_{11}$-epimers like achillin which is the 11(R)-epimer of leucodin (Martinez et al., 1988; Ho et al., 1998), indicating that an enantioselective enzyme that synthesises these $C_{11}$-epimers should exist in these other species. The enzyme exhibits at least some substrate specificity because the $C_{11}$–$C_{13}$ exocyclic double bond of dehydrocostuslacton (18) was not reduced.

The formation of leucodin (22) proves that guaianolides originate from (+)-costunolide. Their formation likely involves more than one enzyme. It was not investigated whether leucodin originates from 11(S),13-dihydrocostunolide (20). Parthenolide (17) is not involved in leucodin biosynthesis, but it cannot be excluded that 11(S),13-dihydroparthenolide is. Various authors have suggested that either 4,5-epoxide or $C_3$-hydroxylation is necessary to direct cyclisation of (+)-costunolide towards a guaiane framework (Brown et al., 1975; Fischer 1990; Teisseire, 1994; Piet et al., 1995, Piet et al., 1996).

Formation of leucodin from (+)-costunolide could be inhibited by the addition of established cytochrome P450 inhibitors or CO, whereas formation of 11(S),13-dihydrocostunolide (20) could not. Furthermore experiments with oxygen-18 demonstrated that the oxygen atom of the keto group also originates from molecular oxygen, which at least suggest the involvement of a cytochrome P450-enzyme in leucodin biosynthesis (West, 1980; Mihaliak et al., 1993).

Leucodin can be regarded as a precursor of 11(S), 13-dihydro-8-deoxylactucin, a minor sesquiterpene lactone of chicory (van Beek et al, 1990). Possibly this sesquiterpene lactone is also formed during the executed incubations, but it is not detected in GC-MS measurement due to its polarity/ lesser volatility. (+)-Costunolide and possibly 11(S), 13-dihydrocostunolide (20) are likely to be involved in the biosynthesis of the other bitter tasting sesquiterpene lactones of chicory. To detect and analyse these compounds in enzymatic reaction mixtures will involve derivatisation and/ or the use of other chromatographic techniques like HPLC.

EXAMPLE 3

Bioconversion of Valencene to Nootkatone Using Enzymes Isolated from Chicory Roots Because of the presence of a cytochrome P450 hydroxylating a sesquiterpenoid skeleton at the C2 position and a dehydrogenase activity that could further oxidize this hydroxy group to form a ketone as demonstrated in Example 2, we decided to investigate the oxidation of the sesquiterpene valencene to study whether nootkatone would be formed.

Synthesis of Reference Compounds

β-Nootkatol was prepared by reduction of 190 mg nootkatone (Fluka) with 20 mg of $LiAlH_4$ in in 5 mL dry ether (diethyl-ether) (Shoji et al., 1984). After stirring the grey suspension for one night, the reaction was stopped by careful addition of $Na_2SO_4.10H_2O$. The mixture was stirred for an additional 30 minutes, and dried by the addition of $MgSO_4$. The solids were filtered off and the ether was washed with distilled water. After drying and evaporation of the solvent, 140 mg of a crude oil was obtained that besides β-nootkatol contained 4% of α-nootkatol, EIMS (70 eV) m/z: 220 [M]$^+$ (33), 177 (77), 161 (40), 145 (52), 131 (77), 119 (100), 109 (41), 107 (50), 105 (59), 95 (46), 93 (60), 91 (43), 81 (45), 79 (80), 77 (64), 69 (47), 67 (52), 55 (58), 43 (55), 41 (94), 39 (54). After flash chromatography of 50 mg from this crude oil on silica with ether-pentane (2:1), fractions devoid of any trace of α:-nootkatol were pooled yielding 3.6 mg of β-nootkatol. $^1H$ NMR (200 MHz, $C_6D_6$) δ 0.83 (d, 3H, J=3 Hz), δ 0.95 (s, 3H), δ 0.96–1.47 (m, 7H), δ 1.75 (m, 3H), δ 1.93 (dt, 1H, J=12.7 and 2.7 Hz), δ 2.07 (m, 1H), δ 2.20–2.33 (m, 2H), δ 4.19–4.26 (m, 1H), δ 4.88 (br s, 2H), 5.44 (br d, 1H). $^{13}$C NMR (100 MHz, DEPT, CDCl$_3$) δ 15.7 (q), δ 18.4 (q), δ 21.1 (q), δ 32.8 (t), δ 33.4 (t), δ 37.8 (t), δ 38.5 (s), δ 39.8 (d), δ 41.3 (d), δ 45.1 (t), δ 68.1 (d), δ 109.2 (t), 125.9 (d), δ 144.9 (s), δ 150.2 (s). EIMS (70 eV) m/z: 220 [M]$^+$ (56), 177 (100), 145 (31), 135 (51), 131 (43), 123 (38), 121 (91), 119 (81), 109 (42), 107 (66), 105 (62), 95 (49), 93 (69), 91 (87), 81 (39), 79 (60), 77 (56), 69 (45), 67 (51) 55 (62), 53 (42), (52), 41 (100), 39 (55).

A mixture of trans,trans-farnesal and cis,trans-farnesal was prepared by dissolving trans,trans-farnesol (Sigma) in pentane and stirring with MnO$_2$. Farnesal was oxidised to a mixture of cis,trans- and trans,trans-farnesoic acid with silver oxide (Caliezi and Schinz, 1947).

Incubations with Microsomal Pellets

Microsomal pellets that contain (+)-germacrene A hydroxylase activity and an enzyme suspension were prepared from deep frozen chicory cubes as described in Example 1. The enzyme suspension was divided in 1 mL aliquots and incubated with 50 µM (+)-valencene in the presence of a 1 mM NADPH-regenerating system that consisted of 1 mM NADPH, 5 mM glucose-6-phosphate, and 1.2 IU glucose-6-phosphate cehydrogenase. The initial concentration of substrate in each assay was 45 µM and all experiments were done in duplicate. To the blank assays no NADPH regenerating system was added, so that cytochrome P450 enzymes (including the (+)-germacrene A hydroxylase) were not active. After 60 minutes the incubations were stopped by storing them at −20° C. in a freezer. The enzyme assays were analysed as described in Example 1.

Results

Figure 17:
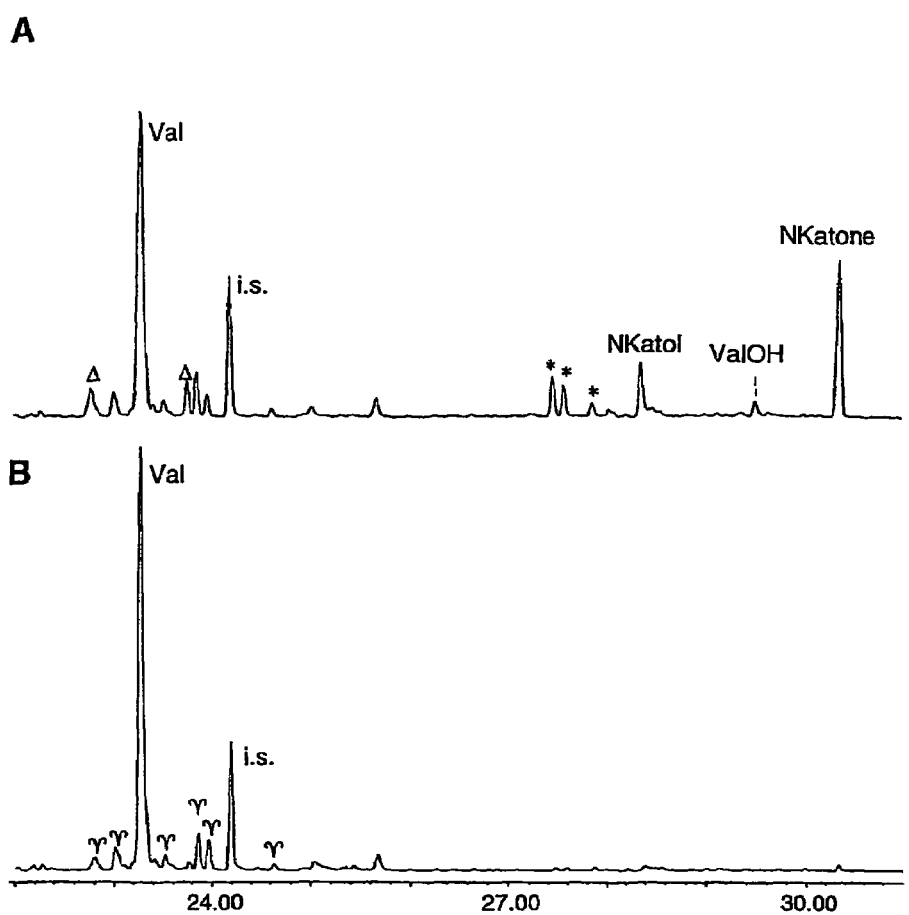
FIG. 17. GC-MS analysis of the products formed by a microsomal preparation of chicory roots incubated with (+)-valencene (Val) in the presence (A) or absence (B) of NADPH. Incubation in the presence of NADPH yields nootkatone (Nkatone), β-nootkatol (Nkatol), and valencene-12-ol (ValOH). Peaks marked with Δ are GC-induced dehydration products of β-nootkatol (M[M]$^+$202). Peaks labelled with an asterisk are sesquiterpene alcohols that presumably origin from enzymatic conversion of sesquiterpene impurities (marked with γ in panel B) present in the commercial sample of (+)valencene used as substrate.

Incubation of (+)-valencene with a microsomal pellet from chicory roots and NADPH yielded (FIG. 17) only a trace of the expected valencene-12-ol ([+]-2-[2R]-2-[1,2,3, 4,6,7,8,8a-octahydro-8α,8aβ-dimethyl-2α-napthalenyl]-2-propen-1-ol) that was identified by comparison of its mass spectrum with a mass spectrum kindly provided by Dr. R. Näf (Firmenich S A, Geneva, Switzerland). EIMS (70 eV) m/z 220 [M]$^+$ (22), 189 (52), 187 (41), 161 (80), 145 (54), 131 (49), 21 (41), 119 (58), 117 (39),107 (55), 105 (84), 95 (44), 93 (73), 91 (100), 81 (47), 79 (84), 77 (51), 67 (39), 55 (48), 41 (63). The major product was nootkatone (Table VII), whereas in most experiments the corresponding β-nootkatol was detected in amounts smaller than the valencene-12-ol (the chromatogram depicted in FIG. 17 is an exception!).

Figure 18:
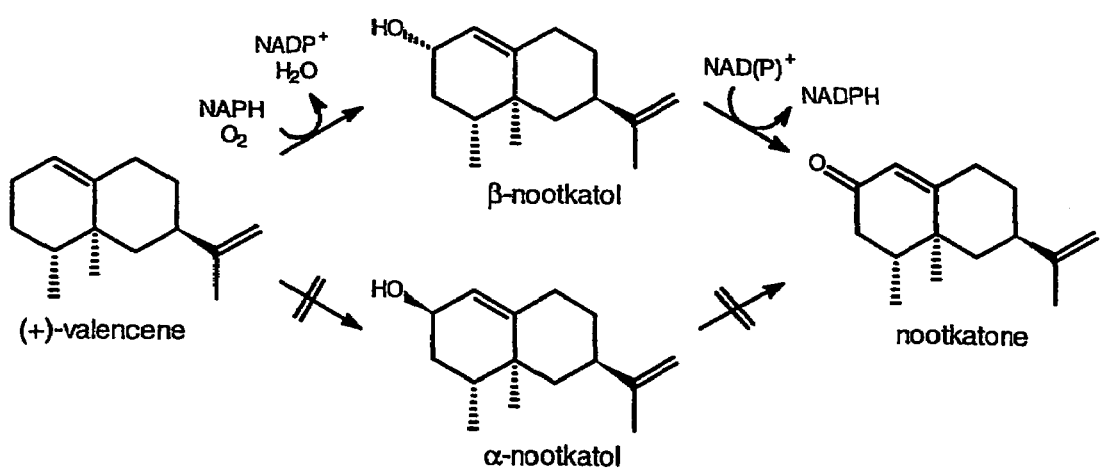
FIG. 18. Conversion of (+)-valencene into nootkatone proceeds via β-nootkatol and not via α-nootkatol.

It was assumed that this β-nootkatol is an intermediate in the formation of nootkatone. For this reason incubations of 100 µM β-nootkatol were performed at pH 10 with NAD (P)$^+$and a 150,000 g supernatant of chicory roots, such as described for the conversion of (−)-elema-1,3,11(13)-12-ol and germacra-1(10),4,11(13)-trien-12-ol by NADP$^+$-dependent dehydrogenases by De Kraker et al. (2001). During incubation the added β-nootkatol was converted for more than 60% into nootkatone in the presence of either 1 mM NADP$^+$ or 1 mM NAD$^+$. In the absence of these cofactors conversion still amounted to 25%, whereas the boiled enzyme extract gave no conversion of β-nootkatol. At pH 7.5, enzyme activity was slightlylower, whereas a 150,000 g pellet, as expected, yielded 3-fold less dehydrogenase activity than the corresponding supernatant. Incubations with a mixture of α- and β-nootkatol showed that only β-nootkatol was converted (FIG. 18).

Figure 19:
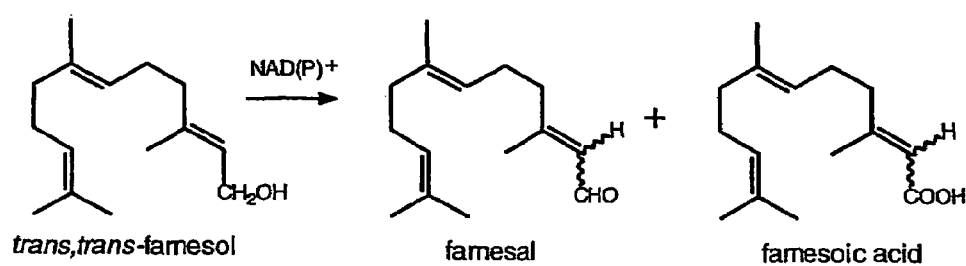
FIG. 19. Conversion of trans,trans-farnesol into farnesal and farnesoic acid by a 150,000 g supernatant of chicory roots in the presence of NADP$^+$.

To get some more information about the substrate specificity of the dehydrogenase(s) present in chicory roots, incubations with the 150,000 g supernatant were also performed with 100 µM trans,trans-farnesol as substrate (FIG. 19) in the presence of either NAD$^+$ or NADP$^+$. Trans,trans-farnesol was converted up to 60% into a mixture of trans, trans-farnesal and cis,trans-farnesal, and small amounts of farnesoic acid were observed as well.

Various pH-values were tested between 7.5 and 11.0 with Tris, glycine and CAPS buffers; the highest conversion of farnesol into farnesal was observed at pH 10 decreasing to 30% of mnaximum enzyme activity at pH 7.0.

Conclusion

Figure 20:
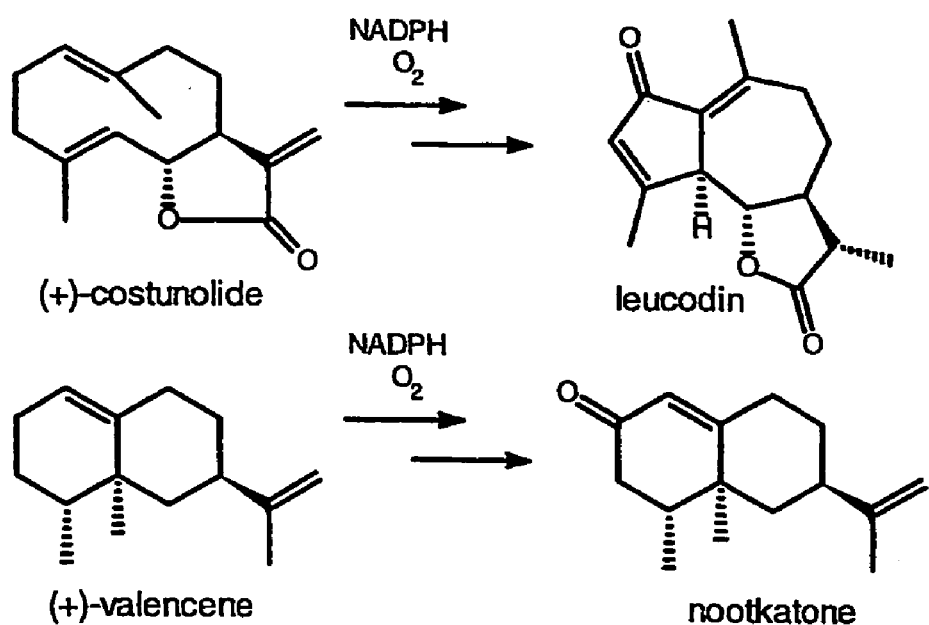
FIG. 20. Similarity between the formation of leucodin in chicory sesquiterpene lactone biosynthesis and the conversion of (+)-valencene to nootkatone by a chicory enzyme preparation.

A chicory enzyme extract efficiently catalysed the conversion of (+)-valencene via β-nootkatol into nootkatone (FIGS. 17 and 18). Possibly these reactions are catalysed by the same enzymes that are involved in the biosynthesis of leucodin from (+)-costunolide (FIG. 20; Example 2). On basis of its structural resemblance with leucodin, the same might have occurred to (+)-ledene (see Example 2, Table I), but this compound was only hydroxylated and not converted into a ketone.

Formation of nootkatone catalysed by enzymes of chicory proceeds via β-nootkatol that is subsequently oxidised to nootkatone by NAD(P)$^+$-dependent dehydrogenase(s). These dehydrogenases are operationally soluble enzymes, but apparently partially end up in the microsomal pellet, just as the germacrene alcohol dehydrogenase(s). The dehydrogenase(s) involved in formation of nootkatone have a strong preference for β-nootkatol over α-nootkatol and this may indicate the involvement of a specific enzyme that perhaps in planta is responsible for the oxidation of the alcohol precursor of leucodin. In generalthe dehydrogenase(s) present in a 150,000 g supernatant of chicory do not seem to act with a high substrate specificity. In addition to the conversion of germacrene alcohol and elemene alcohollaldehyde (Example 1) they are also capable of converting trans,trans-farnesol into farnesal an farnesoic acid. NAD (P)$^+$-dependent oxidation of farnesol to farnesal, including the observed isomerisation of farnesal, has also been reported for other crude plant extracts, (Chayet et al., 1973; Overton and Roberts, 1974). Whether in uivo the isolated dehydrogenase activities are exclusively involved in sesquiterpene lactone biosynthesis or have (also) a different function is uncertain.

Nootkatone is a much sought-after aromatic substance with a distinctive flavor of grapefruit that is widely used in the flavor and fragrance and food industry. Nootkatone was also shown to be an important constituent of anti-ulcer medication (Yamahara et al., 1990). For this reason the possibilities for conversion of the less valuable (+)-valencene has intensively been studied, but the yields obtained by either chemical methods or microbiological methods were not satisfying or too laborious (Dhavlikar and Albroscheit, 1973; Könst et al. 1975; Lamare and Furstoss, 1990). Remarkably, there is not yet any direct proof that in grapefruit, the source of valencene and nootkatone, a biochemical pathway exists for the conversion of (+)-valencene via β-nootkatol into nootkatone (del Rio et al., 1992).

Generally, the production of new materials for flavors and fragrances has been a powerful driving force in the research on the. hydroxylation of terpenes by micro-organisms. Although in some cases successful these microbiological conversions often yield a broad spectrum of products, including epoxides and diols (Lamare and Furstoss, 1990; Drauz and Waldmann, 1995; Faber, 2000) and the oxidations often occur at double bonds. This is in strong contrast to the highly specific oxidation of valencene to nootkatoie as catalysed by the chicory enzyme extract.

EXAMPLE 4

Further Oxidation of Sesquiterpene Alcohols Using Chicory Dehydrogenases

Carboxylic acids are important flavours and fragrances. For instance, fatty acids of various chain lengths are very characteristic for the flavour of cheese (West, 1996), whereas higher fatty acids contribute to the taste and smell of peanuts (Hashim et al., 1993). Branched chain fatty acids are important flavour notes in mutton and sheep cheese (Heinsman, 2000; Heinsman et al., submitted). The chicory dehydrogenases responsible for the conversion of germacrene alcohol to germacrene acid have a rather low substrate specificity. Therefore we have investigated whether these dehydrogenases are capable of oxidising other kinds of terpene alcohols and aldehydes as well as linear and branched aliphatic alcohols and aldehydes.

A chicory enzyme preparation or extract containing the dehydrogenases is made according to De Kraker et al. (2001a). Incubation with an alcohol or aldehyde, for instance amorpha-4,11-diene-12-ol or the corresponding aldehyde, in the presence of $NADP^+$ at pH 10 leads to the formation of the corresponding carboxylic acid in high yield. In case of amorpha-4,11-diene-12-ol, a mixture of artemisinic and dihydroartemisinic acid are produced. Apparently, the dehydrogenases are not only capable of oxidising amorphadiene to artemisinic acid but also the reductase responsible for the reduction of the double bond in the isopropenyl group in the pathway after costunolide (Example 2) is capable of reducing artemisinic acid to dihydroartemisinic acid. As the conversion of dihydroartemisinic acid to artemisinin is supposed to proceed non-enzymatically, chicory may be a suitable production organism for artemisinin, or a source of genes that can be used to produce artemisinin in other organisms.

In the same way, octanol or octanal and 4-methyloctanol or 4-methyloctanal are oxidised to the corresponding octanoic acid and 4-methyloctanoic acid, respectively. Since 4-methyloctanoic acid is chiral, we checked the stereochemical composition of the product, which appears to contain the R-enantiomer in preference.

EXAMPLE 5

Large Scale Bioconversion of Sesquiterpenes Using Enzymes Isolated from Chicory Roots Preparation of Immobilised Enzymes Fresh roots of cultivated chicory are processed as described in Example 1, and the 150,000 g pellets are used for the following experiment. Two grams of pellets are suspended in 50 ml of demineralised water containing 25 mM Tris pH 7.5, 10% glycerol, 1 mM ascorbic acid and 2 mM DTT. To this is added 10 U of an NADPH-regenerating enzyme like glucose 6-phosphate dehydrogenase, hydrogenase, or, preferably, formate dehydrogenase (Seelbach et al., 1996) and 100 g of a solid support like DEAE-Sepharose, polyacrylamide or, preferably, AccurelO beads. The mixture is stirred overnight at 4° C. after which the immobilised enzymes are filtered, washed with demineralised water containing 25 mM Tris pH 7.5, 10 % glycerol and 1 mM ascorbic acid, and stored at 4° C. until usage. Alternatively, the mixture of chicory enzymes and cofactor-recycling enzyme is brought into contact with a hydrophobic membrane (flat membrane or hollow fibre unit) for one night at 4° C., after which the membrane is washed and the membrane (containing the immobilised enzymes) is stored at 4° C. until usage.

Reaction of Immobilised Enzymes with Sesquiterpenes

The inumobilised enzyme is placed in a bioreactor and suspended in 500 ml of demineralised water containing 25 mM Tris pH 7.5, 10% glycerol, and 1 mM ascorbic acid, at room temperature. To this mixture, NADPH is added up to 0.3 mM, together with a suitable amount of cosubstrate, for cofactor recycling. Typically, 1.5 mM of glucose 6-phosphate is added as a cosubstrate when using glucose 6-phosphate dehydrogenase for the recycling of NADPH, whereas 100 mM of formic acid/sodium formate pH 7.5 is added when formate dehydrogenase is the enzyme of choice. Then, the sesquiterpene substrate (100 mM in ethanol) is pumped into the bioreactor at a speed of 0.1 ml/min, under continuous gentle stirring. At the same time, oxygen is pumped into the bioreactor using a thin-walled silicon tube which allows bubble-free aeration (Rissom et al., 1997). This system is chosen since it is known that gas-liquid interfaces Like air bubbles) frequently cause inactivation of monooxygenases. Pumping is stopped when 50 ml of substrate solution (5 mmol, about 1 g of sesquiterpene) has been added, and the reaction mixture is stirred at room temperature until the concentration of product does no longer increase (as monitored by off-line GC). At that time, the immobilised enzyme is ifitered off and the product is obtained by extraction of the aqueous medium with pentane, followed by chromatography over silica (using petroleum ether/ethyl acetate mixtures as the solvents). In this way, 0.5 g of pure hydroxylated sesquiterpene can be obtained, but higher yields are possible, depending on the substrate used. Also nootkatone can be obtained in this way in yields around 50% or higher, using valencene as the substrate. The immobilised enzymes are washed with buffer and can be reused many times. Enzymatic reactions at temperatures higher than ambient are possible but lead to a decreased lifetime of the enzyme preparation.

In case of hydrogenase, more advantageous results are obtained when this enzyme is immobilised separately from the chicory enzymes, and a two-compartment bioreactor is used. The two compartments are separated by a highly porous membrane which is permeable for the NADP(H) cofactor used. One compartment contains immobilised hydrogenase and a thin-walled silicon tube, through which hydrogen gas is pumped. The other compartment contain n the immobilised chicory enzymes and a thin-walled silicon tube, through which oxygen gas is pumped. In this way, both enzymes have access to their substrates and cofactors whereas the hydrogenase does not suffer from inactivation by oxygen.

Alternatively, enzymes that are co-immobilised on solid beads can be used in a fed-batch bioreactor where the outlet is equipped with a hydrophobic membrane such that the product is able to pass whereas the cofactors and the enzymes remain inside the reactor. For this purpose, a membrane reactor in which both enzyme preparations are immobilised on the membrane is most advantageous. Using this system, the enzymes can be used continuously since they are stable for a prolonged period, allowing the facile preparation of several hundred grams of hydroxylated sesquiterpenes or nootkaton.

EXAMPLE 6

Application of Chicory and Other Asteraceae Cell and Hairy Root Cultures for the Bioconversion of (sesqui)terpenes Cultures of de-differentiated cells or callus, hairy roots, shoots and other tissues have been used extensively for the bioconversion of a wide range of substrates. For example cell suspension cultures of grape were able to convert citral to nerol, geraniol and geranylacetate. Also Asteraceae species are suitable for this approach. Hairy root and cell cultures of chicory are obtained using standard protocols (hairy root cultures: Song et al., 1995; cell cultures: Dubois et al., 1988). The cultures are supplied with sesquiterpenes such as valencene, α-gurjunene, amorpha-4,11-diene and α-trans-bergamotene at 200 mg/l. After one week of growth in the presence of the sesquiterpenes, the reaction products are extracted from the culture medium and the hairy roots/cells using pentane/ether. The reaction products are characterised using GC-MS. Incubations with valencene yield an efficient conversion to nootkatone. Incubations with α-gurjunene, amorphadiene and α-trans-bergamotene yield an efficient conversion to the corresponding alcohols with a high regioselectivity: hydroxylation occurs only in the isopropenyl group.

EXAMPLE 7

Isolation and Characterisation of Valencene Synthase from Grapefruit, Pomelo, Orange and *Chamaecyparis nootkatensis*

Recently we have demonstrated that the sesquiterpenoid backbone of the sesquiterpene lactones in chicory is formed by a (+)-germacrene A synthase which cyclizes FPP to (+)-germacrene A (de Kraker et al., 1998; Bouwmeester et al., 1999b). These socalled terpene synthases catalyse the first committed step in all terpenoid biosynthetic pathways. The terpene synthases are a large group of enzymes that all convert the ubiquitous substrates geranyl diphosphate (to the monoterpenes), farnesyl diphosphate (to the sesquiterpenes), geranylgeranyl diphosphate (to the diterpenes) or squalene epoxide (to the triterpenes) (Bohlmann et al, 1998). The sesquiterpenes exhibit an exceptional large structural diversity, and over 7000 different compounds have been described. Like the other terpene synthases (leading to mono-, di- and triterpenes), sesquiterpene synthases exhibit a fair degree of sequence similarity, which allows them—in most cases—to be recognized as a sesquiterpene synthase, and enables the design of degenerate primers to be used in PCR to generate fragments that can be used to screen libraries or can be extended using RACE-PCR to obtain the full-length cDNAs (Bohlmann et al. 1998). Particularly in specialised tissues or enriched libraries also random sequencing may be used to obtain these (sesqui)terpene synthases (Bohlmann et al., 1998).

The valencene synthase gene is isolated from grapefruit, orange, pomelo and *Chamaecyparis nootkatensis* using PCR with degenerate primers based on the sequence homology existing between sesquiterpene synthases (see for example Bouwmeester et al., 1999b) or using the sequence information of the putative sesquiterpene synthase isolated from grapefruit, as published in Genbank (AF411120).

a) Isolation of mRNA. Total RNA is isolated from grapefruit, orange and pomelo albedo and *C. nootkatensis* using the purescript RNA isolation kit (Biozym). DNase I (Deoxyribonuclease I, RNase free) is used to remove DNA from the RNA isolate. The DNase I is removed with a phenol/chloroform extraction after which the RNA is precipitated (ethanol precipitation with NaAc). Poly(A)+RNA is extracted from 20 μg of total RNA using 2 μg poly-d(T)25V oligonucleotides coupled to 1 mg paramagnetic beads (Dynal A.S.). The poly(A)+RNA is resuspended in 20 μl $H_2O$.

b) cDNA Synthesis. The reverse transcription reaction is carried out in a 50 μl reaction containing 10 μl poly (A)+mixture, 0.3 μg oligo $(dT)_{25}V$, 1 mM each dATP, dTTP, dCTP and dGTP, 50 mM Tris-HCl pH 8.3, 80 mM KCl, 10 mM $MgCl_2$ and catalyzed with 12 U AMV reverse transcriptase (Pharmacia). After an incubation for 2 h at 42° C. the reaction is stopped and the cDNA purified with the Wizard PCR Preps DNA purification system (Promega). The cDNA is resuspended in 50 μl $H_2O$.

c) PCR-Based Probe Generation.

Based on comparison of sequences of terpenoid synthases, two degenerated primers were designed for two conserved regions: sense primer: 5'-GAY GAR AAY GGI AAR TTY AAR GA-3'; anti-sense primer: 5'-CC RTA IGC RTC RAA IGT RTC RTC -3' (Wallaart et al., 2001) (primers from Eurogentec, Seraing, Belgium) (Bouwmeester et al., 1999b; Wallaart et al., 2001).

PCR is performed in a total volume of 50 μl containing 0.5 μM of each of the two primers, 0.2 mM DNTP, 1 U Super Taq polymerase/1×PCR buffer (HT Biotechnology LTD, Cambridge, England) and 10 μl cDNA. The reaction mixture is incubated in a. thermocycler (Robocycler, Stratagene) with 1 min denaturation at 94° C., 1.5 min annealing at 42° C. and 1 min elongation at 72° C. during 40 cycles. Agarose gel electrophoresis revealed a single specificPCR product of 550 bp that BLAST comparison shows to have homology with sesquiterpene synthases. The PCR product is purified using the Wizard PCR Preps DNA purification system (Promega) and subcloned using the pGEMT system. *E.coli* JM101 is transformed with this construct. The full length cDNA is obtained using RACE-PCR.

For functional expression, the cDNA clone is subdloned in frame into the expression vector pET 11d (Stratagene). The construct and pET 11d without an insert (as negative control) are transformed to *E.coli* BL 21 (DE3) (Stratagene), and grown overnight on LB agar plates supplemented with ampicillin at 37° C. Cultures of 50 ml LB medium supplemented with ampicillin (100 μg/ml) and 0.25 mM isopropyl-1-thio-β-D-galactopyranoside (IPTG) are occulated with these over night cultures to $A_{600}$=0.5 and grown for 3 h at 27° C. The cells are harvested by centrifugation during 8 minutes at 2000 g and resuspended in 1.2 ml buffer containing 15 mM Mopso (pH 7.0), 10% (v/v) glycerol, 10 mM MgCl2, 1 mM sodium ascorbate and 2 mM DTT (buffer A). The resuspended cells are sonicated on ice during 4 min (5 sec on, 30 sec oft), centrifuged for 5 minutes at 4° C. (14.000 rpm) and the supernatant used for assays.

For determination of product identity, 20 μM [$^3$H]-FDP is added to 0.5 mL of the enzyme preparations diluted 1:1 with buffer A containing 0.1% tween-20. After the addition of a 1-mL redistilled pentane overlay, the tubes are carefully mixed and incubated for 1 h at 30° C. Following the assay, the tubes are mixed, the organic layer is removed and passed over a short column of aluminum oxide overlaid with anhydrous $MgSO_4$. The assay is re-extracted with 1 mL of pentane:diethyl ether (80:20), which is also passed over the aluminum oxide column, and the column washed with 1.5 mL of pentane:diethyl ether (80:20). The extract is analysed using radio-GLC and GC-MS (Bouwmeester et al., 1999a, b). Radio-GLC analysis shows that the cDNA formed a functionally active protein catalysing the formation of one radiolabelled sesquiterpene from [$^3$H]-FDP. The negative control (vector without insert) produced no radioactivity. The samples are also analysed by GC-MS using a HP 5890 series II gas chromatograph equipped with an HP5-MS column (30 m×0.25 mm i.d., 0.25 µm df) and HP 5972A Mass Selective Detector (Hewlett-Packard). The oven is programmed at an initial temperature of 70° C. for 1 min, with a ramp of 5° C. min$^{-1}$ to 210° C. and final time of 5 min. The injection port (splitless mode), interface and MS source temperatures are 150, 290 and 180° C., respectively, and the He inlet pressure is controlled by electronic pressure control to achieve a constant column flow of 1.0 mL min$^{-1}$. Ionization potential is set at 70 eV, and scanning is performed from 30–250 amu. The negative control produced no sesquiterpenes, whereas in assays with the expression products valencene is the major product. The identity of the latter is confirmed by analysis of an authentic standard and comparison of the mass spectra with the authentic standard.

EXAMPLE 8

Isolation of the Genes Encoding Sesquiterpene Hydroxylases and Dehydrogenases from Chicory Two strategies are used to isolate the sesquiterpene hydroxylases and dehydrogenase from chicory. One is based on the presence of sequence homology between P450 genes on the one hand and dehydrogenases on the other. The other method uses random sequencing of a *C. intybus* root cDNA library which has been shown to be a powerful tool for the isolation of biosynthetic genes (Aharoni, et al., 2000).

a). Isolation of mRNA. Total RNA is isolated from chicorychicons using the purescript RNA isolation kit (Biozym). DNase I (Deoxyribonuclease I, RNase free) is used to remove DNA from the RNA isolate. The DNase I is removed with a phenol/chloroform extraction after which the RNA is precipitated (ethanol precipitation with NaAc). Poly(A)+RNA is extracted from 20 µg of total RNA using 2 µg poly-d(T)25V oligonucleotides coupled to 1 mg paramagnetic beads (Dynal A.S.). The poly(A)+RNA is resuspended in 20 µl H$_2$O.

b) cDNA Synthesis. The reverse transcription reaction is carried out in a 50 µl reaction containing 10 µl poly (A)+mixture, 0.3 µg oligo (dT)$_{25}$V, 1 mM each dATP, dTTP, dCTP and dGTP, 50 mM Tris-HCl pH 8.3, 80 mM KCl, 10 mM MgCl$_2$ and catalyzed with 12 U AMV reverse transcriptase (Pharmacia). After an incubation for 2 h at 42° C. the reaction is stopped and the cDNA purified with the Wizard PCR Preps DNA purification system (Promega). The cDNA is resuspended in 50 µl H$_2$O.

c) PCR-Based Probe Generation.

Based on comparison of sequences of cytochrome P450 and dehydrogenase enzymes, degenerate primers are designed for conserved regions such as the ER targeting signal, the heme-binding domain, the central region of helix I and the PERF-motif. PCR is performed in a total volume of 50 µl containing 0.5 µM of each of the two primers, 0.2 mM dNTP, 1 U Super Taq polymerase/1×PCR buffer (HT Biotechnology LTD, Cambridge, England) and 10 µl cDNA. The reaction mixture is incubated in a thermocycler (Robocycler, Stratagene) with 1 min denaturation at 94° C., 1.5 min annealing at 42° C. and 1 min elongation at 72° C. during 40 cycles. Agarose gel electrophoresis revealed a single specific PCR product.

d) cDNA Library Construction and Screening.

A cDNA library is constructed using the UniZap XR custom cDNA library service (Stratagene). For library screening 200 ng of the PCR amplified probes are gel-purified, randomly labelled with [α-$^{32}$P]dCTP, according to manufacturer's recommendation (Ready-To-Go DNA labelling beads (–dCTP), Pharmacia) and used to screen replica filters of 10$^4$ plaques of the cDNA library plated on *E.coli* XL1-Blue MRF' (Stratagene). The plaque lifting and hybridization are carried out according to standard protocols. Positive clones are isolated using a second and third round of hybridization. In vivo excision of the pBluescript phagemid from the Uni-Zap vector is performed according to manufacturer's instructions (Stratagene).

In addition, 1500 clones from the cDNA library are randomly sequenced and compared to sequences in the databases using BLAST. Promising P450 and dehydrogenase-like sequences were found and are further characterised by heterologous expression.

Expression of the Isolated Genes in *E. coli* and Yeast. For functional expression, the cDNA clones are subcloned into suitable expression vectors and transformed to a suitable expression host. Induced cells are harvested by centrifugation during 8 minutes at 2000 g and resuspended in 1 ml assay buffer. The resuspended cells are either sonicated on ice during 4 min (5 sec on, 30 sec off), centrifuged for 5 minutes at 4° C. (14.000 rpm) and the supernatant used for assays or used as intact cells. In both systems germacrene A, valencene and nootkatol are used as substrates. Ether extracts of the assays are analysed using GC-MS (see Example 7). The negative control produced no germacrene A alcohol nootkatol or nootkatone, whereas in assays with the expression products of both genes conversion of germacrene A to germacrene A alcohol, valencene to nootkatol and of nootkatol to nootkatone, respectively, occurred.

EXAMPLE 9

Transformation of Chicory with the Valencene or Amorrhadiene Synthase Gene to Obtain Nootkatone or Artemisinin Producing Chicory Chicory Transformation. Chicory is transformed as described in PCT/EP00/02130 (Bouwmeester et al., 1999b) with a construct harboring the valencene or amorphadiene synthase. After regeneration, transgenic plants are screened for the activity of the introduced gene by examining sesquiterpene synthase activity in enzyme extracts. Hereto, 100 mg of tissue, ground in liq N$_2$, is extracted in a 2-ml Eppendorf vial, using a plastic probe to further homogenize the tissue, in 1.0 ml of extraction buffer containing containing 50 mM Mopso (pH 6.8), 20% (v/v) glycerol, 50 mM sodium ascorbate, 50 mM NaHSO$_3$, 1% PVP-40, 10 mM MgCl$_2$ and 5 mM DTT. After extraction, the samples are centrifuged for 20 min at 20,000 g at 4° C. 0.5 mL of the supernatant are diluted 2-fold with buffer A (Example 7) also containing 6 mM sodium orthovanadate (an inhibitor of phosphohydrolase activity). After addition of 20 µm $^3$H-FPP and a 1 mL redistilled pentane overlay, the tubes are carefully mixed and incubated for 1 h at 30° C. The assays are extracted and analysed using radio-GC and GC-MS as described for Example 7.

The wildtype and GUS-construct controls all exhibit a similar sesquiterpene synthase activity, which is due to the presence of endogenous germacrene A synthase activity. The transformants exhibit analtered sesquiterpene profile, with varying amounts of valencene and amorphadiene, respectively in addition to germacrene A. For some transformants 90% of the in vitro produced sesquiterpene is valencene.

Extracts of the transgenic plants that were analysed using GC-MS showed the presence of valencene, nootkatol and nootkatone on the one hand and artemisinic acid, dihydroartemisinic acid and artemisinin on the other hand, respectively.

EXAMPLE 10

Expression of Valencene Synthase, Sesquiterpene Lactone C2 Hydroxylase and Corresponding Dehydrogenase in Micro-Organisms for the Production of Nootkatone

*Saccluzromyces cereuisiae* and *Pichia pastoris* are transformed using the *S. cerevisae* EasyComp™ transformation kit (Invitrogen) according to manufacturer's instructions with constructs harboring:
1. the valencene hydroxylase and a general, commercial or chicory dehydrogenase
2. the valencene synthase and valencene hydroxylase
3. the valencene synthase, valencene hydroxylase and general, commercial or chicory dehydrogenase Transgenic cells are grown in a reactor, and products of the cells are analysed after extraction.

Transgenic yeast cells harboring constructs 2 and 3 produce nootkatone, showing that the yeast dehydrogenases oxidise the nootkatol produced (in 2). Yeast cells harboring construct 1 produce nootkatone upon feeding of valencene.

EXAMPLE 11

Expression of Sesquiterpene Synthases, and Sesquiterpene Hydroxylases in Micro-organisrns for the Production of Regio- and Stereospecific Sesquiterpene Alcohols

*Saccharomyces cerevisiae* and *Pichia pastoris* are transformed using the *S. cereuisae* EasyComp™ transformation kit (Invitrogen) according to manufacturer's instructions with a construct harboring a sesquiterpene synthase, such as, but not limited to, amorphadiene synthase, (−)-α-transbergamotene synthase, alloisolongifolene synthase, γ-gurjunene synthase and a sesquiterpene hydroxylase cDNA (obtained as described in Example 8).

Transgenic cells are grown in a reactor, and products of the cells are analysed after extraction.

Transgenic yeast cells are harboring the constructs produce amorphadien-12-ol, (E)-trans-bergamota-2,12-dien-14-ol; alloisologifolene alcohol; and 5,11(13)-guaiadiene-12-ol, respectively.

References

Ando M, Ibayashi K, Minami N, Nakamura T, Isogai K (1994) Studies on the synthesis of sesquiterpene lactones, 16. The synthesis of 11β,13-dihydrokauniolide, estafiatin, isodehydrocostuslactone, 2-oxodesoxyligustrin, arborescin, 1,10-epiaborescin, 11β,13-dihydroludartin, 8-desoxy-11β,13-dihydrorupicolin B, 8-deoxyrupicolin B, 3,4epiludartin, ludartin, kauniolide, dehydroleucodin and leucodin. J Nat Prod 57: 443–445

Aharoni A, Keizer L C P, Bouwmeester H J, Zhongkui Sun, Alvarez-Huerta M, Verhoeven H A, Blaas J, van Houwelingen A M M L, de Vos R C H, van der Voet H, Jansen R C, Guis M, Davis R W, Schena M, van Tunen A J, O'Connell A P (2000) Identification of the SAAT gene involved in strawberry flavor biogenesis by using DNA microarrays. The Plant Cell 12: 1–16.

Asakawa Y (1982) Chemical constituents of hepaticae. In W Herz, H Grisebach, G W Kirby, eds, Progress in the Chemistry of Organic Natural Products Vol. 42. Springer Verlag, Wien—N.Y.

Asakawa Y, Matsuda R, Takemoto T (1980) Mono and sesquiterpenoids from *Wiesnerella denudate*. Phytochemistry 19: 567–569.

Balkrishna B L, Childers W E, Pinnick J R, Pinnick H W (1981) Oxidation of α,β-unsaturated aldehydes. Tetrahedron 37: 2091–2096

Barton D H R, Moss G P, Whittle J A (1968) Investigations on the biosynthesis of steroids and terpenoids part I: A preliminary study of the biosynthesis of santonin. J Chem Soc (C) 1813–1818

Bawdeekar A S, Kelkar G R (1965) Terpenoids—LXVIII: Structure and absolute configuration of costic acid—a new sesquiterpene acid from costus root oil. Tetrahedron 21: 1521–1528

Bawdekar A S, Kelkar G R, Bhattacharyya S C (1967) Terpenoids—CIV: Costol fraction of costus root oil. Tetrahedron 23: 1993–1996

Birch A J (1974) Dihydrobenzenes in synthesis in terpenen related areas. J Agric Food Chem 22: 162–167

Bohlman F, Ates N, Jakupovic J (1983) Hirsutinolides from South African *Vernonia* species. Phytochemistry 22: 1159–1162

Bohlmann J, Meyer-Gauen G, Croteau R (1998) Plant terpenoid synthases: Molecular biology and phylogenetic analysis. Proceedings of the National Academy of Science, USA 95: 4126–4133

Bouwmeester H J, Wallaart T E, Janssen M H A, van Loo B, Jansen B J M, Posthumus M A, Schmidt C O, de Kraker J-W, Konig W A, Franssen M C R (1999a) Amorpha-4, 11-diene synthase catalyses the first probable step in artemisinin biosynthesis. Phytochemistry 52: 843–854

Bouwmeester H J, Kodde J, de Kraker J W (1999b) Sesquiterpenoid synthase genes and their use for influencing bitterness and resistance in plants. Patent PCT/EP00/02130

Brown E D, Sutherland J K, Sam T W (1975) Medium-ring 1,5-dienes. Part III. Cyclization of germacra-1(10),4,7-(11)-triene oxides. J Chem Soc Perlin Trans I, 2332–2336

Caliezi A, Schinz H (1947) Zur Kenntnis der Sesquiterpene und Azulene: die Cyclisation der Farnesylsäure. Helv Chim Acta 32: 2556–2560

Chayet L, Pont-Lezica R, George-Nascimiento C, Cori O (1973) Biosynthesis of sesquiterpene alcohols and aldehydes by cell free extracts from orange flavedo. Phytochemistry 12: 95–101

Cordell G A (1976) Biosynthesis of sesquiterpenes. Chem Rev 76: 425–460

De Kraker J W, Franssen M C R, de Groot Ae, König W A, Bouwmeester H J (1998) (+)-Germacrene A biosynthesis. The committed step in the biosynthesis of bitter sesquiterpene lactones in chicory. Plant Physiol. 117: 1381–1392.

De Kraker J W, Franssen M C R, Daln M C F, de Groot Ae, Bouwmeester H J (2001a) Biosynthesis of germacrene A carboxylic acid in chicory: Demonstration of a cytochrome P450 (+)-germacrene A hydroxylase and NADP$^+$/NAD$^+$-dependent sesquiterpenoid dehydrogenase(s) involved in sesquiterpene lactone biosynthesis. Plant Physiol. 125: 1930–1940.

De Kraker J W, Franssen M C R, de Groot Ae, Shibata T, Bouwmeester H J (2001b) Germacrenes from fresh costus roots. *Phtytochemistry,* 58:481–487.

del Rio J A, Ortunio A, Garcia-Puig D, Porras I, Garcia-Lidón A, Sabater F (1992) Variations of nootkatone and valencene levels during the development of grapefruit. J Agric Food Chem 40: 1488–1490

Dhavalikar R S, Rangachari P N, Bhattacharyya P K (1966) Microbiological tranrformations of terpenes: Part IX—Pathways of degradation of limonene in a soil pseudomonad. Indian J Biochem 3: 158–164

Dhavlikar R S, Albroscheit G (1973) Microbiologische Umsetzung von Terpenen: Valencen. Dragoco Report 12: 250–258

Donaldson R P, Luster D G (1991) Multiple forms of plant cytochromes P-450. Plant Physiol 96: 669–674

Drauz K, Waltmainn H (1995) Enzyme Catalysis in Organic Synthesis—A Comprehensive Handbook. VCH, Weinheim, 667–701

Faber K (2000) Biotransformations in Organic Chemistry. $4^{nd}$ ed, Springer-Verlag, Berlin, 453 pages.

Fischer N H (1990) Sesquiterpene lactones: Biogenesis and biomimetic transformations. In G Towers and H Towers, eds, Biochemistry of the Mevalonic Acid Pathway to Terpenoids. Plenum Press, New York, pp 161–201

Fischer N H, Olivier E J, Fischer H D (1979) The biogenesis and chemistry of sesquiterpene lactones. In W Herz, H Grisebach, G W Kirby, eds, Progress in the Chemistry of Organic Natural Products Vol. 38. Springer Verlag, Wien—N.Y.

Franssen M C R, Walton N J (1999) Biotransformations. In N J Walton, D E Brown eds, Chemicals from Plants, World Scientific Publishers, London, 277–325

Geissman T A (1973) The biogenesis of sesquiterpene lactones of the compositae. In V C Runeckles, T J Marby, eds, Recent Advances in Phytochemistry, Vol 6, Academic Press, New York and Londen, pp 65–95

Genderen, H van, Schoonhoven L M, Fuchs A (1996) Chemisch-ecologische flora van Nederland en België. Een inleiing over aard en ecologische betekenis van secundaire plantenstoffen, H van Genderen, L M Schoonhoven, A Fuchs, eds. KNNV Uitgeverij, Utrecht, 298 pp Grieco P A, Nishazawa M (1977) Total synthesis of (+)-costunolide. J Org Chem 42: 1717–1720

Halkier B A (1996) Catalytic reactivities and structure/function relationships of cytochrome P450 enzymes. Phytochemistry 34: 1–21

Harborne J B, Baxter H, Moss G P (1999) Phytochemical Dictionary. A handbook of bioactive compounds from plants, $2^{nd}$ edition. Taylor & Francis Hashim I B, Koehler P E, Kvien C K (1993) Fatty acid composition, mineral content, and flavor quality of southern runner peanuts treated with herbicides and fungicides. Peanut Sci. 20: 106–111

Heinsman N W T J (2000) Lipase-catalyzed kinetic resolution of branched chain fatty acids and their esters. PhD thesis, Wageningen University Heinsinan N W J T, Franssen M C R, van der Padt A, Boom R M, van't Riet K, de Groot Ae Lipase-mediated resolution of branched chain fatty acids. Biocatal. Biotransform., submitted Herz W (1977) Sesquiterpene lactones in the compositae. In V H Heywood, J B Harborne, B L Turner, eds, The Biology and Chemistry of the Compositae. Academic Press, London, pp 337–357

Ho C, Choi E J, Yoo G S, Kim T M, Ryu S Y (1998) Desacetylmatricin, an anti-allergic component from Taraxacum platycarpum. Planta Med 64: 577–578

Holland H L (1992) Organic Synthesis with Enzmes. VCH Publishers, New York, pp 29–31

Hunter G L K, Brogden V B Jr (1965) Conversion of valencene to nootkatone. J Food Sci 30: 876–878

Jain T C, Banks C M, McCloskey J E (1970) Dehydrosaussurea lactone and reversibility in the germacranolide-cope reaction. Tetrahedron Lett 11: 841–844

Jerussi A R (1970) Selective oxidations with selenium dioxide. In Selective Organic Transformations. Wiley-Interscience, p. 301–313.

Karp F. Mihaliak C A, Harris J L, Croteau R (1990) Monoterpene biosynthesis: specificity of the hydroxylations of (–)-limonene by enzyme preparations from peppermint (Mentha piperita), spearmint (Mentha spicata) and perilla (Perilla frutescens) leaves. Arch Biochem Biophys 276: 219–226

Kesselmans R P W (1992) Total synthesis of all stereoisomers of eudesm-11-en-14-ol. PhD thesis, Wageningen University Könst W M B, van der Linde L M, Witteveen J G (1975) Recent developments in the chemistry of eremophilanes. International Flavours and Food Additives 6: 121–125

Kupchan S M, Fessler D C, Eakin M A, Giacobbe T J (1970) Reactions of alpha methylene lactone tumor inhibitors with model biological nucleophils. Science 168: 376–377

Lamare V, Furstoss R (1990) Bioconversion of sesquiterpenes. Tetrahedron 46: 4109–4132

March J (2001) Advanced Organic Chemistry: reactions, mechanisms and structure. $5^{th}$ ed, Wiley-Interscience, New York, N.Y., 2083 pages Martinez M, Munoz-Zamora A, Joseph-Nathan P (1988). Conformational analysis of achillin and leukodin. J Nat Prod 51: 221–228

Mathews C E, Van Holde H E (1996) Biochemistry. $2^{nd}$ ed, Oregon State University, The Benjamin/ Cummings Publishing Company Maurer B, Grieder A (1977) Sesquiterpenoids from costus root oil (Saussurea lappa Clarke). Helv Chim Acta 60: 2177–2190

Meijer A H (1993) Cytochrome P-450 and secondary metabolism in Catharanthus roseus. Ph.D. thesis, Leiden University Mihaliak C A, Karp F, Croteau (1993) Cytochrome P-450 terpene hydroxylases. In P. J. Lea ed, Methods in Plant Biochemistry, Enzmes of Secondary Metabolism, Vol 9. Academic Press, Londen, pp 261–279

Minnaard (1997) Germacrene sesquiterpenes: synthesis and role in biosynthesis. PhD thesis. Wageningen University.

Miyazawa M, Honjo Y, Kameoka H (1998) Bioatransforamtion of the sesquiterpenoid (+)-γ-gurjunene using a plant pathogenic fungus Glomerella cingulata, as a biocatalyst. Phytochemstry 49: 1283–1285

Overton K R, Roberts F M (1974) Interconversion of trans,tranis and cis,trans farnesol by enzymes from Andographis. Phytochemistry 13: 95–101

Paul A, Bawdekar A S, Joshi R S, Somesekar Roa A, Kelkar G R, Bhattacharyya S C (1960) Terpenoids XX: examination of costus root oiL Perf and Ess Oil Rec 15: 115–120

Pesaro M, Bozzato G, Schudel P (1968) The total synthesis of racemic nootkatone. Chem Commun 1152–1154

Petersen M, Seitz H U (1988) Reconstitution of cytochrome P-450-dependent digitoxin 12β-hydroxylasefrom cell cultures of foxglove (Digitalis lanata EHRH.). Biochem J 252: 537–543

Petersen M, Alfermann A W, Reinhard E, Seitz H U (1987) Immobilization of digitoxin 12β-hydroxylase, a cytochrome $P^{-45}$-dependent enzyme from cell cultures of Digitalis lanata EHRH. Plant Cell Rep 6: 200–203

Petit F, Furstoss R (1995) Synthesis of (1S,5R)-2,8-dioxabicyclo[3.3.0]octan-3-one from its enantiomer: a subunit of clerodane derivatives. Synthesis 1517–1520

Picman A K (1986) Review article number 7: biological activities of sesquiterpene lactones. Biochem Syst Ecol 14: 255–281

Piet D P, Franssen M C R, de Groot Ae (1996) Biotransformation of allylically activated (E,E)-cyclodeca-1,6-dienols by *Cichorium intybus*. Tetrahedron 52: 11273–11280

Piet D P, Schrijvers R, Franssen M C R, de Groot Ae (1995) Biotransformation of germacrene epoxides by *Cichorium intybus* L. Tetrahedron 51: 6303–6314

Price K R, DuPont M S, Shepherd R, Chan H W-S, Fenwick G R (1990) Relationship between the chemical and sensory properties of exotic salad crops—colored lettuce (*Lactuca satiua*) and chicory (*Cichorium intybus*). J Sci Food Agric 53: 185–192 Pyrek J S T (1985) Sesquiterpene lactones of *Cichorium intybus* and *Leontodon autumnalis*. Phytochemistry 24: 186–188

Reichardt P B, Anderson B J, Claus en T P, Hoskins L C (1988) Thermal instability of germacrone: implications for gas chromatographic analysis of thermally unstable analytes. Can J Chem 67: 1174–1177

Rissom S, Schwarz-Linek U, Vogel M, Tishkov V I, Kragl U (1997) Synthesis of chiral ε-lactones in a two-enzyme system of cyclQhexanone mono-oxygenase and formate dehydrogenase with integrated bubble-free aeration. Tetrahedron: Asymmetry 8: 2523–2526

Sannai A, Fujimori T, Kato K (1982) Studies on flavor components of roasted chicory root. Agric Biol Chem 46: 429–433

Schuler M A (1996) Plant cytochrome P450 monooxygenases. Crit Rev Plant Sci 15: 235–284

Seaman F C (1982) Sesquiterpene lactones as taxonomic characters in the Asteraceae. Bot Rev 48: 124–145

Seelbach K, Riebel B, Hummel W, Kula M R, Tishkov V I, Egorov A M, Wandrey C, Kragl U (1996) A Novel, Efficient Regenerating Method of NADPH Using a New Formate Dehydrogenase. Tetrahedron Lett 37: 1377–1380

Seigler D S (1995) Plant Secondary Metabolism. KIuwer Academic Publishers, Boston/Dordrecht/London, 759 pp Seto M, Miyase T, Umehara K, Ueno A, Hirano Y, Otani N (1988) Sesquiterpene lactones from *Cichorium endivia* L and *C. intybus* L and cytotoxic activity. Chem Pharm Bull 36: 2423–2429

Shoji N, Umeyama A, Asakawa Y, Takemoto T, Nomoto K, Ohizumi Y (1984) Structural determination of nootkatol, a new sesquiterpene isolated from *Alpina oxyphylla* Miquel possessing calcium-antagonistic activity. J Pharm Sc 73: 843–844

Somasekar Roa A, Kelkar G R, Bhattacharyya S C (1960) Terpenoids—XXI: the structure of costunolide, a new sesquiterpene lactone from costus root oil. Tetrahedron 9: 275–283

Song Q, Gomez-Barrios M L, Hopper E L, Hjortso M A, Fischer N H (1995) Biosynthetic studies of lactucin derivatives in hairy root cultures of *Lactuca floridana*. Phytochemistry 40: 1659–1665

Suga, T. and Hirata, T. (1990) Biotransformation of exogenous substrates by plant cell cultures. Phytochemistry 29: 2393–2406.

Takasugi M, Okinaka S, Katsui N, Masamune T, Shirata.A, Ohuchi M (1985) Isolation and structure of lettucinin A, a novel guaianolide phytoalexin from *Lactuca sativa* var. *capitata* (Compositae). J Chem Soc Chem Commun 621–622

Takeda, K (1974) Stereospecific Cope rearrangement of the germacrene-type sesquiterpenes. Tetrahedron 30: 1525–1534

Teisseire P J (1994) Chemistry of Fragrant Substances. VCH Publishers Inc., New York, pp 193–289

Umbreit M A. Sharpless K B (1977) Allylic oxidation of olefins by catalytic and stoichiometric selenium dioxide with tert-butyl hydroperoxide. J Am Chem Soc 99: 5526–5528 van Beek T A, Maas P, King B M, Leclercq E, Voragen A G J, de Groot Ae (1990) Bitter sesquiterpene lactones from chicory roots. J Agric Food Chem 38: 1035–1038

Vogel G, Hartinan H D, Krahnstover K (1994) Handbuch des speziellen Gemüisebaues. Ulmer, Stuttgart, pp 84–144

Wallaart T E, Bouwmeester H J, Hille J, Poppinga L, Maijers N C A (2001) Amorpha-4,11-diene synthase: cloning and functional expression of a key enzyme in the biosynthetic pathway of the novel antimalarial drug artemisinin. Planta 212: 460–465.

Walton N J, Brown D E (1999) eds, Chemicals from plants: perspectives on plant secondary metabolism. World Scientific Publishers, Singapore, 425 pages Weeda E J, Westra R, Westra C H, Westra C (1991) Nederlandse oecologische flora: wilde planten en hun relaties 4. IVN, Amsterdam, pp 152–154

West C A (1980) Hydroxylases, monooxygenases, and cytochrome P-450. In D D Davis, ed, The Biochemistry of Plants, Vol 2. Academic Press, Londen, pp 317–342

West S (1996) Flavour production with enzymes. In: Industrial Enzymology, Godfrey T and West S, eds, $2^{nd}$ ed, Macmillan Press Ltd, London, UK, p. 209–225.

Wilson C W III, Shaw P E (1978) Synthesis of nootkatone from valencene. J Agric Food Chem 26: 1430–1432

Yamahara J, Hao Y, Tamrai Y (1990) Anti-ulcer effect in rats of bitter cardamom constituents. Chem Pharm Bull 38: 3053–3054.

The invention claimed is:

1. A method for the conversion of valencene to nootkatone comprising:
   a. contacting valencene with chicory root extract, whereby said valencene is converted to nootkatone, and
   b. recovering said nootkatone.

2. A method for the conversion of amorpha-4,11-diene to amorpha-4,11-dien-12-ol comprising:
   a. contacting amorpha-4,11-diene with chicory root extract, whereby said amorpha-4,11-diene is converted to amorpha-4,11-dien-12-ol, and
   b. recovering said amorpha-4,11-dien-12-ol.

3. A method for the conversion of (+)-γ-gurjunene to 5,11(13)-guaiadiene-12-ol comprising:
   a. contacting (+)-γ-gurjunene with chicory root extract, whereby said (+)-γ-guriunene is converted to 5,11(13)-guaiadiene-12-ol, and
   b. recovering said 5,11(13)-guaiadiene-12-ol.

4. A method for the conversion of α-trans-bergamotene to (E)-trans-bergamota-2,12-dien-14-ol, comprising:
   a. contacting α-trans-bergamotene with chicory root extract, whereby said α-trans-bergamotene is converted to (E)-trans-bergamota-2,12-dien-14-ol, and
   b. recovering said (E)-trans-bergamota-2,12-dien-14-ol.

5. A method for the conversion of alloisologifolene to alloisologifolene alcohol, comprising:
   a. contacting alloisologifolene with chicory root extract, whereby said alloisologifolene is converted to alloisologifolene alcohol, and
   b. recovering said alloisologifolene alcohol.

* * * * *

UNITED STATES PATENT AND TRADEMARK OFFICE
CERTIFICATE OF CORRECTION

PATENT NO.        : 7,214,507 B2                                    Page 1 of 1
APPLICATION NO.   : 10/489762
DATED             : May 8, 2007
INVENTOR(S)       : Bouwmeester et al.

It is certified that error appears in the above-identified patent and that said Letters Patent is hereby corrected as shown below:

Column 3, Line 52   Now reads:   "germacra-1(10),4, 11(i3)-trien-12-oic"

Should read: --germacra-1(10),4, 11(13)-trien-12-oic--

Column 32, Line 60  Now reads:   "research on the. hydroxylation"

Should read: --research on the hydroxylation--

Signed and Sealed this

Eighteenth Day of September, 2007

JON W. DUDAS
*Director of the United States Patent and Trademark Office*